US010709515B2

(12) United States Patent
Griffiths et al.

(10) Patent No.: US 10,709,515 B2
(45) Date of Patent: *Jul. 14, 2020

(54) METHODS OF CONTROLLING MOTION OF UNDER-ACTUATED JOINTS IN A SURGICAL SET-UP STRUCTURE

(71) Applicant: Intuitive Surgical Operations, Inc., Sunnyvale, CA (US)

(72) Inventors: Paul G. Griffiths, Santa Clara, CA (US); Paul W. Mohr, Mountain View, CA (US); Brandon D. Itkowitz, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/002,509

(22) Filed: Jun. 7, 2018

(65) Prior Publication Data
US 2018/0280098 A1 Oct. 4, 2018

Related U.S. Application Data

(63) Continuation of application No. 15/126,536, filed as application No. PCT/US2015/020896 on Mar. 17, 2015, now Pat. No. 10,022,196.
(Continued)

(51) Int. Cl.
*A61B 34/32* (2016.01)
*A61B 34/35* (2016.01)
(Continued)

(52) U.S. Cl.
CPC .............. *A61B 34/35* (2016.02); *A61B 34/30* (2016.02); *A61B 34/37* (2016.02); *B25J 9/02* (2013.01);
(Continued)

(58) Field of Classification Search
USPC .................................................. 700/245–264
See application file for complete search history.

(56) References Cited

U.S. PATENT DOCUMENTS

| 4,604,787 A | * | 8/1986 | Silvers, Jr. | ......... | B23Q 3/15526 29/26 A |
| 5,279,309 A | * | 1/1994 | Taylor | ................... | A61B 34/20 600/595 |

(Continued)

FOREIGN PATENT DOCUMENTS

| CN | 101421080 A | 4/2009 |
| CN | 102625670 A | 8/2012 |

(Continued)

OTHER PUBLICATIONS

Extended European Search Report for Application No. 15765509.3, dated Oct. 18, 2017, 15 pages.
(Continued)

*Primary Examiner* — Jonathan L Sample
(74) *Attorney, Agent, or Firm* — Kilpatrick Townsend & Stockton LLP

(57) ABSTRACT

Robotic and/or surgical devices, systems, and methods include kinematic linkage structures and associated control systems configured to control movement of passive or under-actuated joints by coordinated joint braking of the under-actuated joints concurrent with driving of one or more driven joints. In one aspect, the methods include driving a set-up structure by pivoting an orienting platform supporting multiple manipulators back-and-forth in opposite directions while selectively braking the under-actuated joints to inhibit passive joint movement away from a reference joint state and releasing braking to facilitate movement of the joints toward the reference until each of the under-actuated joints of the multiple manipulators are at the respective reference states. In another aspect, a joint brake controller is provided
(Continued)

that receives a motor torque input and converts the input to a brake control input by determining an impulse applied variable braking to deplete the impulse over time.

25 Claims, 17 Drawing Sheets

Related U.S. Application Data

(60) Provisional application No. 61/954,537, filed on Mar. 17, 2014.

(51) Int. Cl.
| | |
|---|---|
| *A61B 34/30* | (2016.01) |
| *A61B 34/37* | (2016.01) |
| *B25J 9/02* | (2006.01) |
| *B25J 9/16* | (2006.01) |
| *A61B 90/00* | (2016.01) |
| *A61B 90/50* | (2016.01) |

(52) U.S. Cl.
CPC ....... B25J 9/1694 (2013.01); *A61B 2090/035* (2016.02); *A61B 2090/508* (2016.02); *Y10S 901/01* (2013.01); *Y10S 901/02* (2013.01); *Y10S 901/46* (2013.01)

(56) References Cited

U.S. PATENT DOCUMENTS

| | | | |
|---|---|---|---|
| 5,377,310 A | 12/1994 | Jain et al. | |
| 5,784,542 A * | 7/1998 | Ohm | B25J 3/04 700/247 |
| 5,923,139 A * | 7/1999 | Colgate | B25J 9/1656 318/566 |
| 6,120,433 A * | 9/2000 | Mizuno | A61B 34/70 600/102 |
| 6,393,340 B2 * | 5/2002 | Funda | B25J 9/1648 318/568.1 |
| 6,434,507 B1 * | 8/2002 | Clayton | A61B 17/32002 600/104 |
| 6,441,577 B2 | 8/2002 | Blumenkranz et al. | |
| 6,645,196 B1 * | 11/2003 | Nixon | B25J 9/1664 128/898 |
| 7,883,458 B2 * | 2/2011 | Hamel | A61B 17/32002 600/1 |
| 8,357,144 B2 * | 1/2013 | Whitman | A61B 10/0233 128/898 |
| 8,423,182 B2 * | 4/2013 | Robinson | A61B 34/25 700/245 |
| 8,672,837 B2 * | 3/2014 | Roelle | A61B 1/00006 600/118 |
| 8,749,190 B2 * | 6/2014 | Nowlin | B25J 9/1682 318/568.21 |
| 10,022,196 B2 | 7/2018 | Griffiths et al. | |
| 2002/0032452 A1 * | 3/2002 | Tierney | G06Q 30/02 606/130 |
| 2005/0193451 A1 * | 9/2005 | Quistgaard | A61B 5/6843 414/1 |
| 2006/0106493 A1 * | 5/2006 | Niemeyer | A61B 34/70 700/245 |
| 2007/0142825 A1 * | 6/2007 | Prisco | A61B 34/76 606/1 |
| 2007/0299427 A1 * | 12/2007 | Yeung | B25J 9/047 606/1 |
| 2008/0046122 A1 * | 2/2008 | Manzo | A61B 1/00149 700/245 |
| 2008/0200794 A1 * | 8/2008 | Teichman | A61B 90/39 600/407 |
| 2009/0062813 A1 * | 3/2009 | Prisco | A61B 34/37 606/130 |
| 2009/0076476 A1 * | 3/2009 | Barbagli | A61B 5/1076 604/500 |
| 2009/0163929 A1 * | 6/2009 | Yeung | B25J 9/047 606/130 |
| 2010/0228264 A1 * | 9/2010 | Robinson | A61B 34/76 606/130 |
| 2010/0228588 A1 * | 9/2010 | Nielsen | G06Q 10/06 705/7.11 |
| 2010/0274087 A1 * | 10/2010 | Diolaiti | A61B 34/37 600/118 |
| 2011/0082452 A1 * | 4/2011 | Melsky | A61B 18/24 606/15 |
| 2011/0295248 A1 * | 12/2011 | Wallace | B25J 9/1689 606/33 |
| 2011/0319714 A1 * | 12/2011 | Roelle | A61B 1/00006 600/118 |
| 2011/0319815 A1 * | 12/2011 | Roelle | A61B 1/00149 604/95.01 |
| 2014/0031983 A1 * | 1/2014 | Low | B25J 13/025 700/257 |
| 2014/0039517 A1 * | 2/2014 | Bowling | A61B 34/30 606/130 |
| 2014/0052153 A1 * | 2/2014 | Griffiths | A61B 34/70 606/130 |
| 2014/0052154 A1 | 2/2014 | Griffiths et al. | |
| 2014/0222207 A1 * | 8/2014 | Bowling | A61B 17/16 700/261 |

FOREIGN PATENT DOCUMENTS

| | | |
|---|---|---|
| JP | 2007307399 A | 11/2007 |
| KR | 20110030034 A | 3/2011 |
| WO | WO-2011109041 A1 | 9/2011 |
| WO | WO-2011143338 A1 | 11/2011 |

OTHER PUBLICATIONS

International Search Report and Written Opinion for Application No. PCT/US2015/20896, dated Jul. 17, 2015, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner (detail of Block A in FIG. 14A)

*(detail of Block B in FIG. 14B)*

METHODS OF CONTROLLING MOTION OF UNDER-ACTUATED JOINTS IN A SURGICAL SET-UP STRUCTURE

CROSS REFERENCE TO RELATED APPLICATIONS

This application is a Continuation of U.S. Ser. No. 15/126,536 filed Sep. 15, 2016 (Allowed); which is a U.S. National Stage application of PCT/US2015/020896 filed Mar. 17, 2015; which claims priority to U.S. Provisional Application No. 61/954,537 filed Mar. 17, 2014, the contents of which are incorporated herein by reference in their entirety for all purposes.

This application is generally related to U.S. application Ser. No. 13/967,573 entitled "Movable Surgical Mounting Platform Controlled by Manual Motion of Robotic Arms," filed Aug. 15, 2013 (now U.S. Pat. No. 9,259,281), and U.S. application Ser. No. 13/967,594 entitled "User Initiated Break-Away Clutching of a Surgical Mounting Platform," filed Aug. 15, 2013 (now U.S. Pat. No. 9,452,020), the entire contents of which are incorporated herein by reference in their entireties for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or tele-surgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new tele-surgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up in deployment and stowing, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved robotic and/or surgical devices, systems, and methods. Kinematic linkage structures and associated control systems described herein are particularly beneficial in helping system users to arrange the robotic structure in preparation for use, including deploying structures in preparation for a surgical procedure on a particular patient or stowing structures after use. Exemplary robotic surgical systems described herein may have one or more kinematic linkage sub-systems that are configured to help align a manipulator structure with the surgical work site. The joints of these set-up systems may be actively driven, passive (so that they may be manually articulated and then locked into the desired configuration while the manipulator is used therapeutically), or a mix of both. Embodiments of the robotic systems described herein may employ a set-up mode in which one or more joints are actively driven to effect passive movement of one or more other joints of the kinematic chain and selectively brake the one or more other joints so as to control the passive movement so as to move the joints to reference joint states. In many embodiments, the one or more other joints are passive set-up joints and the reference joint states correspond to a desired configuration of a manipulator arm or multiple manipulator arms associated with the set-up joints. In many embodiments, the actively driven joints will move a platform structure that supports multiple manipulators, which in turn moves associated set-up joints by controlled passive joint movement to certain reference joint states, thereby facilitating and expediting the arrangement of the overall system into a desired orientational and/or positional configuration with the workspace. Advantageously, this approach allows reconfiguration of the system by controlling movement of under-actuated set-up joints, without requiring manual manipulation of the joints. In addition, the set-up joints of multiple arms can be controlled simultaneously allowing for reconfiguration using passive set-up joints in less time than would typically be possible by manual articulation alone. Optionally, movement of an orienting platform can result in movement of a set-up joint linkage disposed between a manipulator and the platform, as well as movement of set-up joint linkages associated with additional manipulator assemblies supported by the platform. Control of the passive movement of one or more set-up joints may be achieved by selective braking of one or more joint brakes corresponding to the set-up joints in response to a sensed joint state of the respective set-up joints.

Thus, in a first aspect, a method for preparing for robotic surgery is provided. The method includes sensing a displacement of one or more set-up joints of a first robotic manipulator from an initial position to a reference position that corresponds to a desired configuration of the manipulator or multiple manipulators, calculating a movement of a set-up structure linkage that imparts force and/or movement to linkages associated with the set-up joints that move the set-up joints towards the respective reference positions by passive joint movement, and controlling passive joint movement of the set-up joints by selective braking until the set-up joints reach the reference location. Selective braking controls passive movement of the set-up joints by inhibiting passive movement away from the reference position and facilitating passive movement toward the reference position. Once the set-up joint is at the reference position, the brake can be applied to lock the set-up joint in place.

In many embodiments, the set-up structure linkage may include a mounting base, a column, a member, and an extendable boom. The column may be slideably coupled with the mounting base. Additionally, the column may be selectively positioned relative to the mounting base along a first support axis that is vertically oriented. The member may be a boom base member rotationally coupled to the column through a shoulder joint. The member may be selectively oriented relative to the column around a second support axis that is vertically oriented. The extendable boom may be slideably coupled with the member to selectively position the extendable boom relative to the member along a third support axis that is horizontally oriented. The orienting platform may be rotationally coupled to the extendable boom member. The calculated driven joint movements may include a movement of any of a plurality of joints of the set-up structure linkage that are driven so as to impart forces and/or moments in more distal linkages that move one or more under-actuated joints to a desired reference state or position.

In one aspect, the processor includes non-transitory machine readable code embodying instructions for determining selective braking of one or more under-actuated joints based on a sensed joint state of the under-actuated joints and an error between an initial state of the joint and a reference state. In many embodiments, the system may utilize a proportional derivative controller to determine a torque control input required to move the under-actuated joint to the reference state and employ a joint brake controller that integrates the torque control input to determine an impulse over time in response to a sensed torque in an under-actuated joint to determine a braking control input that selectively applies a joint brake of the joint to deplete the sensed joint torque according to the impulse over time based on a relationship between braking and joint torque (often over several cycled movements of the driven joints). In some aspects, the joint controller is configured to determine the braking control input so that the torque is depleted over time so as to provide a substantially constant velocity during passive movement of the joint and/or to provide a constant deceleration of the joint during passive movement, which in some embodiments may be based on a magnitude of the displacement of the under-actuated joint from the reference state.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1:
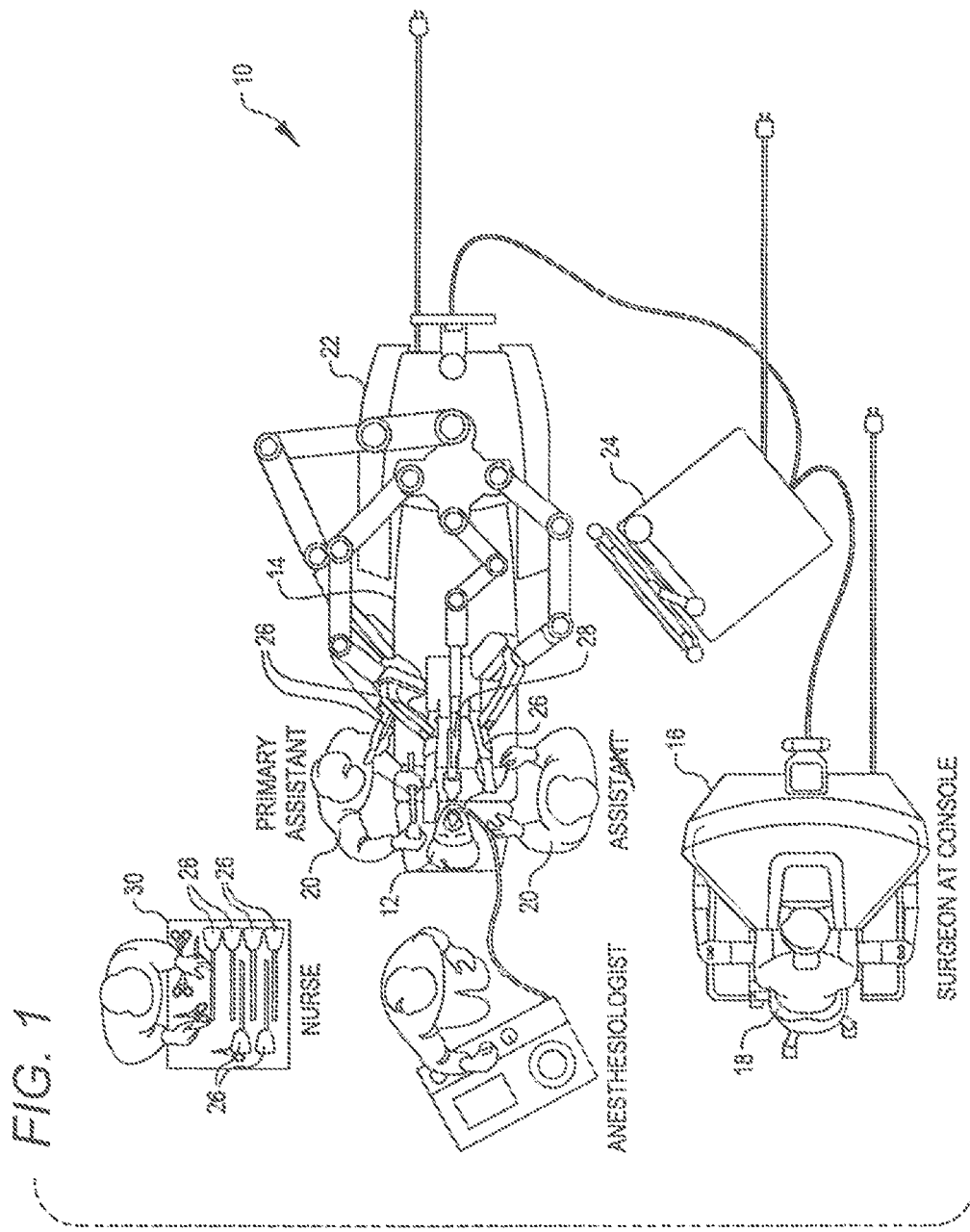
FIG. 1 is a plan view of a minimally invasive robotic surgery system being used to perform a surgery, in accordance with some embodiments of the invention.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. Along with actively driven manipulators used to interact with tissues and the like during treatment, robotic surgical systems may have one or more kinematic linkage systems that are configured to support and help align the manipulator structure with the surgical work site. These set-up systems may be actively driven or may be passive, so that they may be manually articulated and then locked into the desired configuration while the manipulator is used therapeutically. The passive set-up kinematic systems may have advantages in size, weight, complexity, and cost. Since a plurality of manipulators may be used to treat tissues of each patient, the challenges of quickly arranging the robotic system in preparation for surgery can be significant.

One option is to mount multiple manipulators to a single platform, with the manipulator-supporting platform sometimes being referred to as an orienting platform. The orienting platform can be supported by an actively driven support linkage (sometimes referred to herein as a set-up structure, and typically having a set-up structure linkage, etc.) The system may also provide and control motorized axes of the robotic set-up structure supporting the orienting platform with a user control, or typically are automatic according to a sensed configuration and the desired configuration associated with the reference states.

To maintain the advantages of both passive and actively-driven joints of the robotic manipulators, embodiments of the robotic systems described herein may employ a mode in which one or more joints are actively driven to elicit a particular response in one or more passive set-up joints distal of the actively driven joints by passive joint movement to achieve desired reference states of the passive set-up joints. The passive joint movement of these set-up joints may be controlled through selective application of joint brakes, inhibiting passive movement away from the reference states and facilitating passive joint movement toward the reference state until the set-up joints arrive at the respective reference states. The reference state may refer to any or all of a desired location within the work space, a desired location relative to certain other joints of the system, a desired velocity and an acceleration in a particular direction.

In certain aspects, the actively driven joints will automatically move a platform-supporting linkage structure that supports multiple manipulators that move continuously between opposing directions in one or more degrees of freedom to elicit the desired movement of one or more passive joints without requiring manual articulation. By controlling passive movement of under-actuated joints by selective braking, the system greatly facilitates the arrangement of the overall system by concurrently moving one or more set-up joints supporting each manipulator to move the manipulators into a desired configuration, orientation and/or positional alignment with the workspace. The desired configuration, orientation or alignment may include any number of arrangements. In some embodiments, the desired arrangement includes any of a deployed arrangement, a stowed arrangement or a partially stowed arrangement. In the deployed configuration, the manipulators are extended into the workspace for set-up of the manipulators, which may include interchanging of surgical tools on one or more manipulators. In the stowed and partially stowed configurations, the manipulators may be contracted and folded against one another, at least partly, so as to occupy less of the workspace. Independent positioning of one, some or all of the manipulators supported by the platform can optionally be provided through controlled movement of passive set-up joint systems supporting one, some, or all of the manipulators relative to the platform by utilizing aspects of the methods described herein.

In one aspect, methods in accordance with the invention achieve controlled movement of set-up joints through inertial effects and controlled braking of the joints. For example, the set-up joints described herein that support the surgical robotic arms (e.g. slave manipulators) are typically used for set-up of the robotic system for surgery and for stowing the robotic arms of the system after surgery, such that these joints are moved infrequently and there is little need for such joints to be motor driven. These set-up joints are configured as passive joints with joint brakes, such that the joints can freely float to allow passive movement of the joints during manual manipulation of the robotic arms during set-up or stowing and can be locked into position by applying the respective joint brake. It is desirable in certain scenarios to move the robotic arms to pre-determined locations to aid draping of the robotic arms in preparation for surgery, patient cart roll-up, and stowing of the robotic arms after a surgical procedure. The example methods described herein allow for controlled movement of these passive set-up joints, without requiring manual movement of such joints, by moving a platform linkage (e.g. orienting platform), the common base on which the set-up joints of the robotic arms are mounted and by selectively controlling application of the joint brakes of the set-up joints.

In certain aspects, methods include a set-up joint brake controller that exploit the passive dynamics of the set-up joint linkages. For example, the orienting platform upon which the set-up joints are mounted can be commanded through a trajectory inducing acceleration by moving the orienting platform through the driving of one or more driven joints that control movement of the orienting platform. The brake controller of the set-up joint receives the state of its associated set-up joint (such as through a joint state sensor), a reference state of the set-up joint (position, velocity, and/or acceleration) and the acceleration of the orienting platform. When the inertia of the set-up joint linkage and the acceleration of the orienting platform, in combination, is sufficient to cause the set-up joint link to accelerate towards the reference, the joint brake is released. In certain aspects, the joint brake determines whether the brake is released partially or fully based on a sensed joint state of its respective joint. For example, if the joint velocity drops to zero or is opposite the desired direction of motion of the set-up joint, the brake may be applied until the acceleration of the orienting platform is favorable. The joint brake controller may also be configured so the joint brake is applied when the reference state is reached to lock its respective joint at the desired position. In another aspect, the brake controller can be configured to control the passive movement of the passive joint as it moves toward the reference state. For example, if the velocity of the passive joint exceeds a reference velocity, partial brake application can arrest the velocity of the associated linkage so as to provide smoother, more favorable movement of the set-up joint to the desired position.

The above described aspects of the present invention are particularly useful in methods that provide for deployment and stowing of multiple robotic arms in a tele-surgical operation system, such as any of those described in detail herein. Many such systems include robotic arms having one or more passive set-up joints that assist in set-up and stowing of the robotic arms. The workflow of setting up, operating and stowing the robotic arms often requires the robotic arms to be placed in certain stowed and deployed configurations. While this can be accomplished by manual movement of the under-actuated set-up joints, this approach can be problematic. For example, in such systems, a user must generally manually release the set-up joint brakes and manually move the various joints of each robotic arm, which can be time consuming and significantly diminish the system's ease of use. Furthermore, should the device need to be reconfigured or partially stowed during a procedure, when the robotic arms may be draped with sterile drape, the methods described herein allows a surgeon or use in a non-sterile area to control movement of the passive set-up joints and reconfiguring or partially stowing the robotic arms. It is appreciated that these methods may be used to control passive movement of a joint using inertial forces imposed thereon by driving of another joint in combination with joint braking of the subject joint. Systems in which such methods may be applied are described in detail below.

Minimally Invasive Robotic Surgery

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
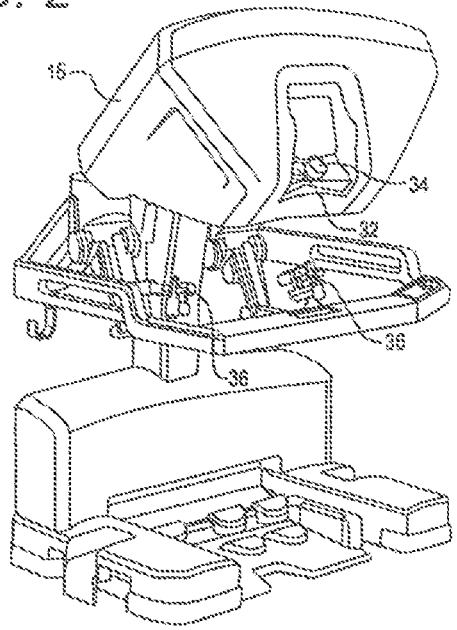
FIG. 2 is a perspective view of a surgeon's control console for a robotic surgery system, in accordance with some embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with tele-presence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
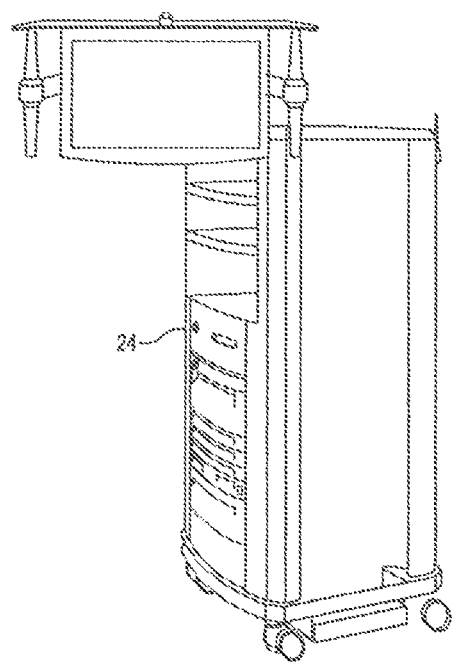
FIG. 3 is a perspective view of a robotic surgery system electronics cart, in accordance with some embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
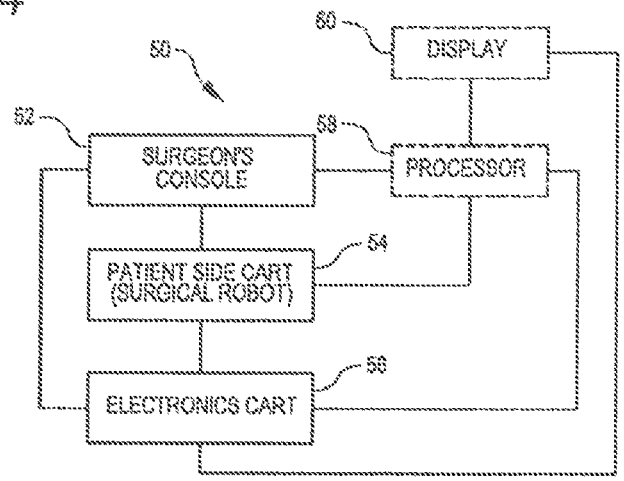
FIG. 4 diagrammatically illustrates a robotic surgery system, in accordance with some embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media, and could also comprise a monolithic code but will more typically comprise a number of subroutines, optionally running in any of a wide variety of distributed data processing architectures.

Figure 5A:
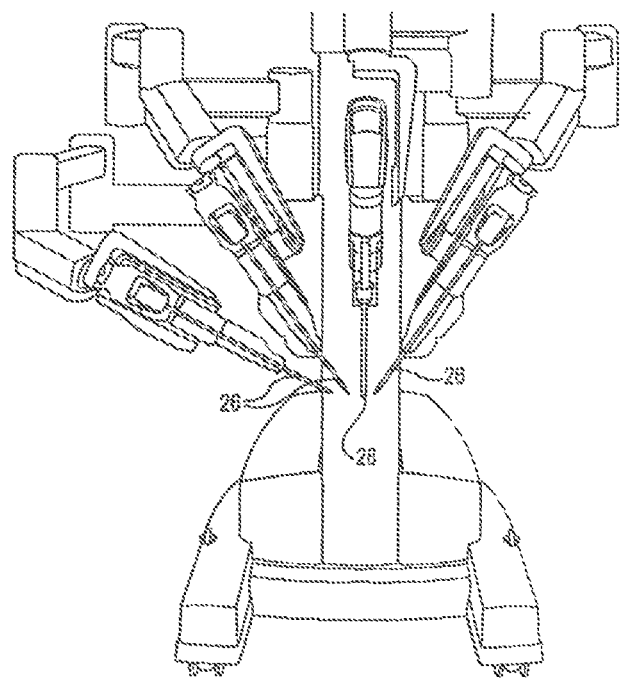
FIG. 5A is a partial view of a patient side cart (surgical robot) of a robotic surgery system, in accordance with some embodiments.
Figure 5B:
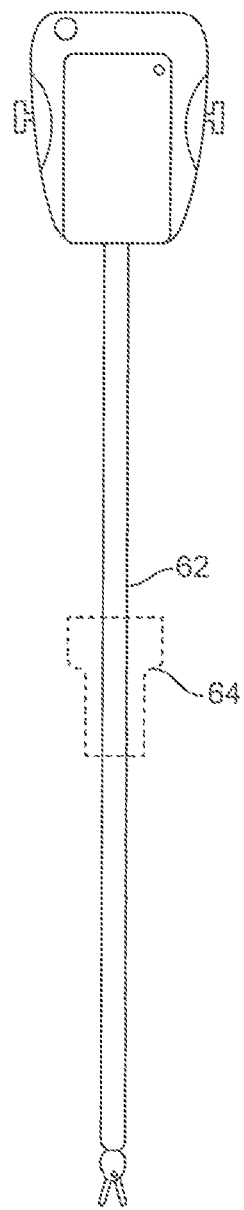
FIG. 5B is a front view of a robotic surgery tool, in accordance with some embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
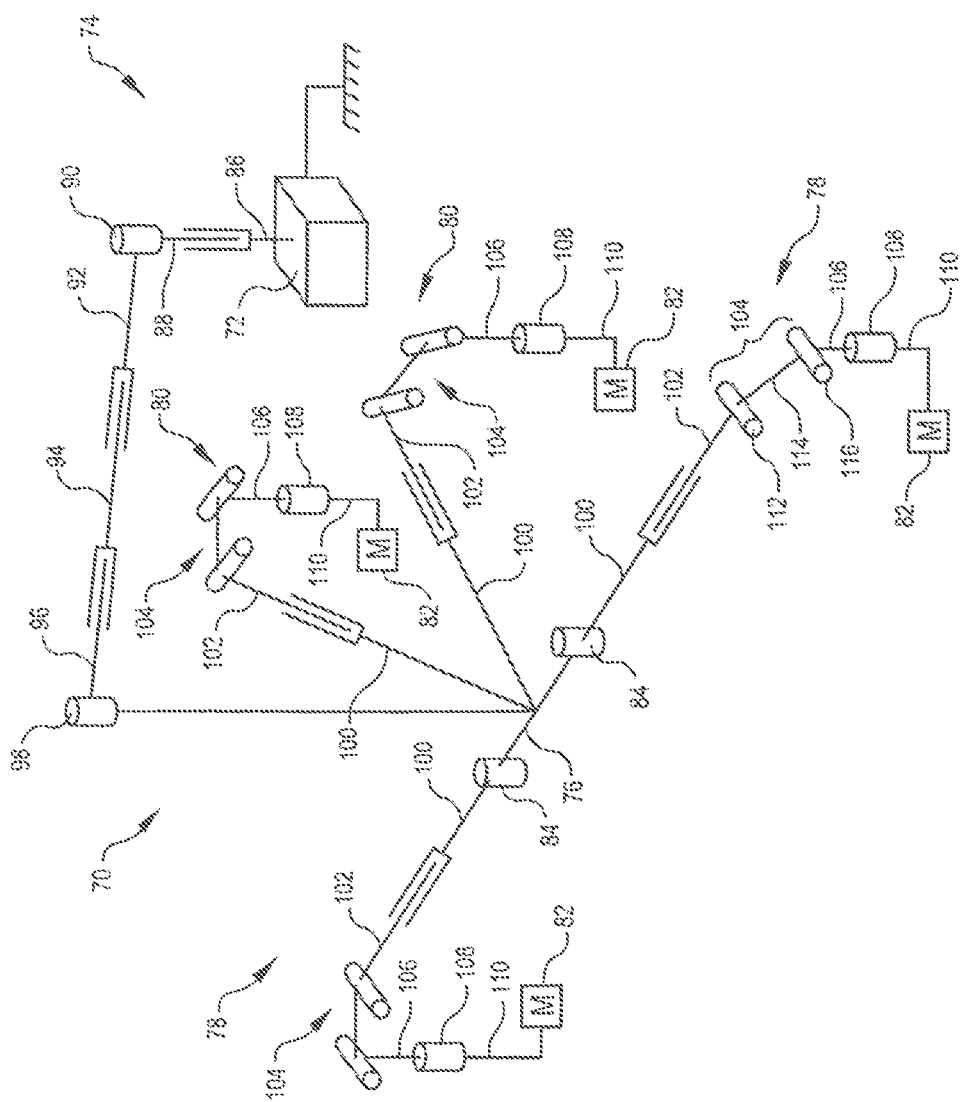
FIG. 6 is a perspective schematic representation of a robotic surgery system, in accordance with some embodiments.

FIG. 6 is a perspective schematic representation of a robotic surgery system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage portions 104 configured and operable to selectively translate the set-up linkage vertical link 106 in a vertical direction while keeping the set-up linkage vertical link 106 vertically oriented. In example embodiments, each of the set-up linkage portions 104 includes a first joint 112, a coupling link 114, and a second linkage 116. The first joint 112 rotationally couples the coupling link 114 to the set-up linkage extension link 102. The second joint 116 rotationally couples the set-up linkage vertical link 106 to the coupling link 114. The first joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
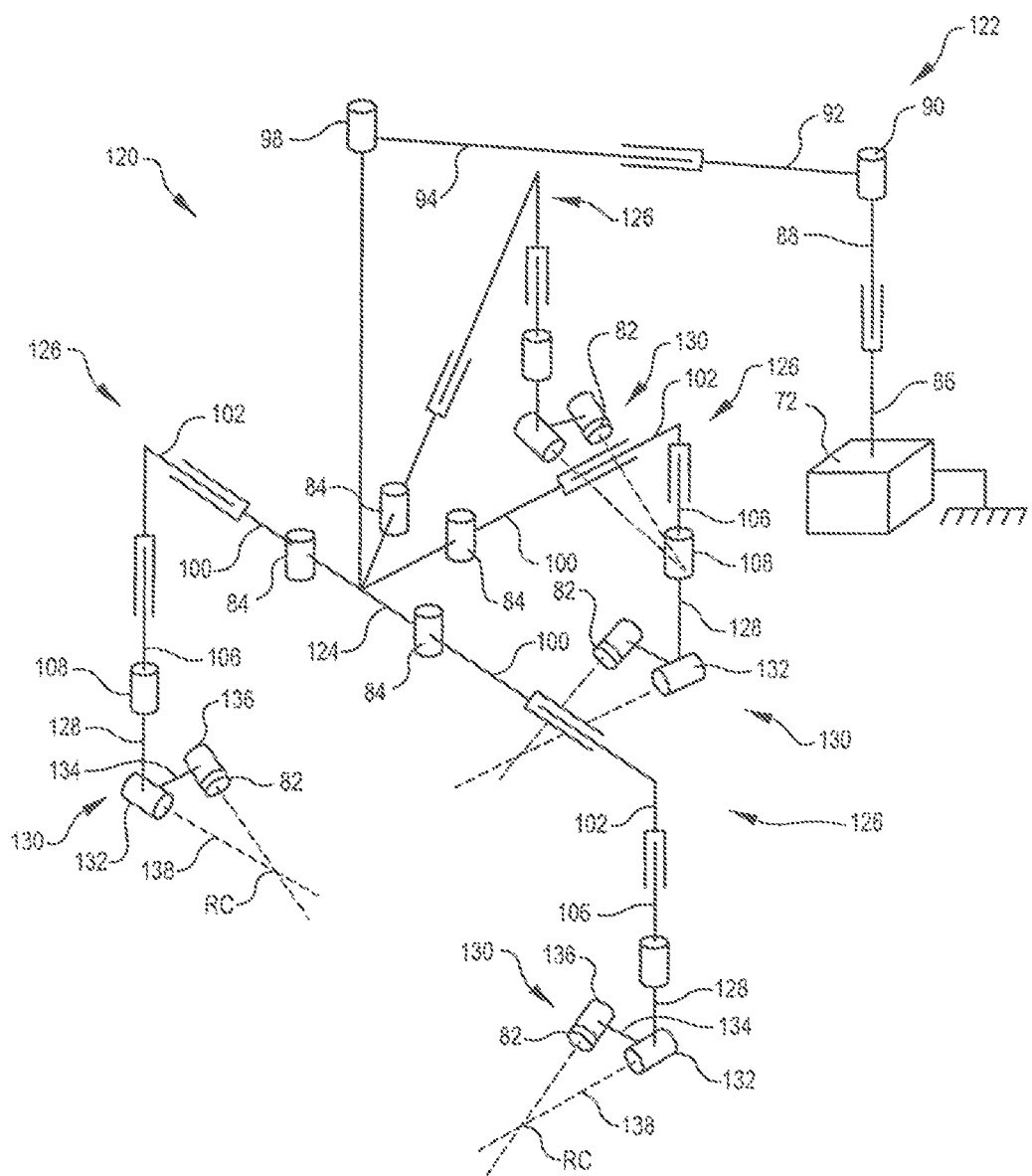
FIG. 7 is a perspective schematic representation of another robotic surgery system, in accordance with some embodiments.

FIG. 7 is a perspective schematic representation of a robotic surgery system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
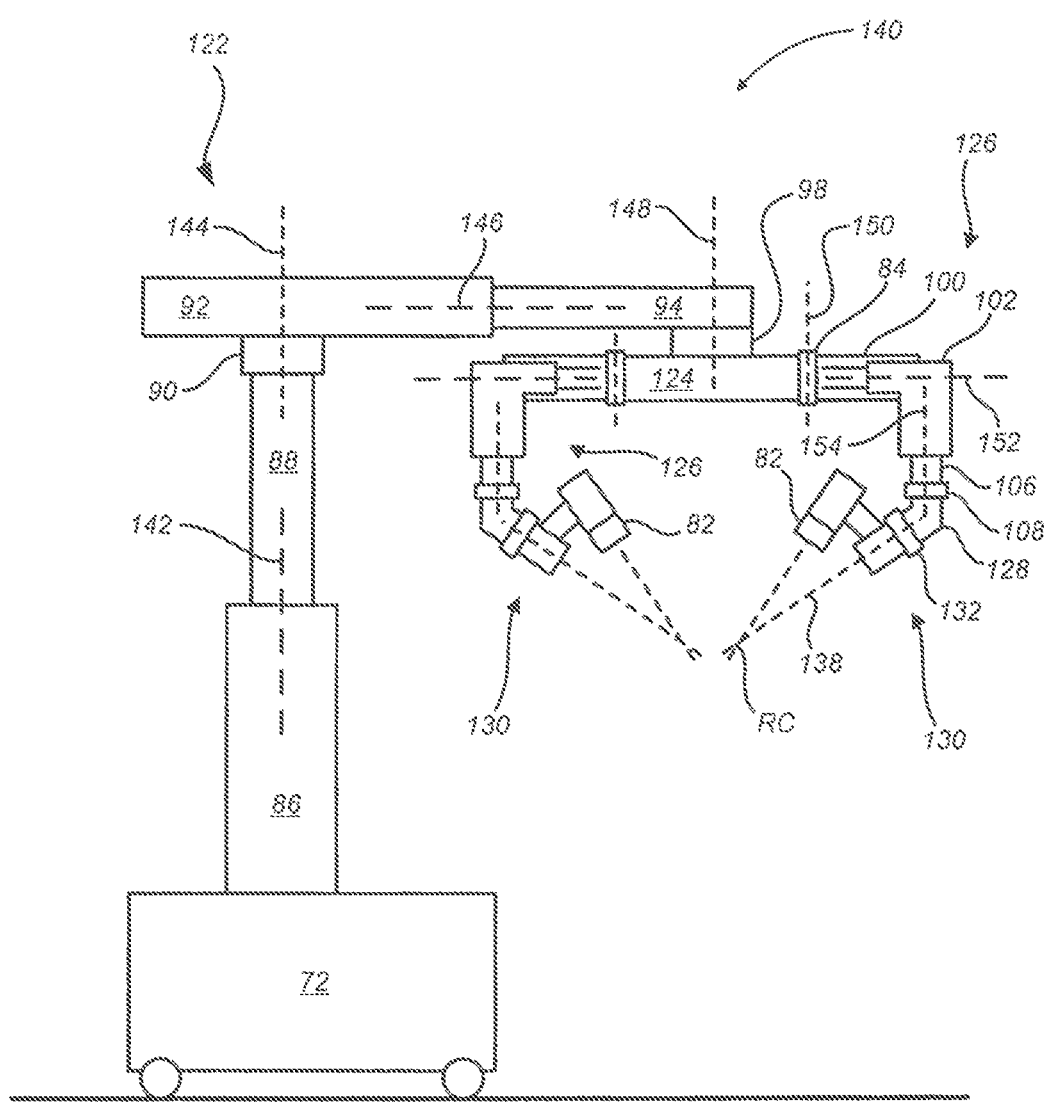
FIG. 8 shows a robotic surgery system, in accordance with many embodiments, in conformance with the schematic representation of FIG. 7.

FIG. 8 is a simplified representation of a robotic surgery system 140, in accordance with many embodiments, in conformance with the schematic representation of the robotic surgery system 120 of FIG. 7. Because the surgery system 140 conforms to the robotic surgery system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9A:
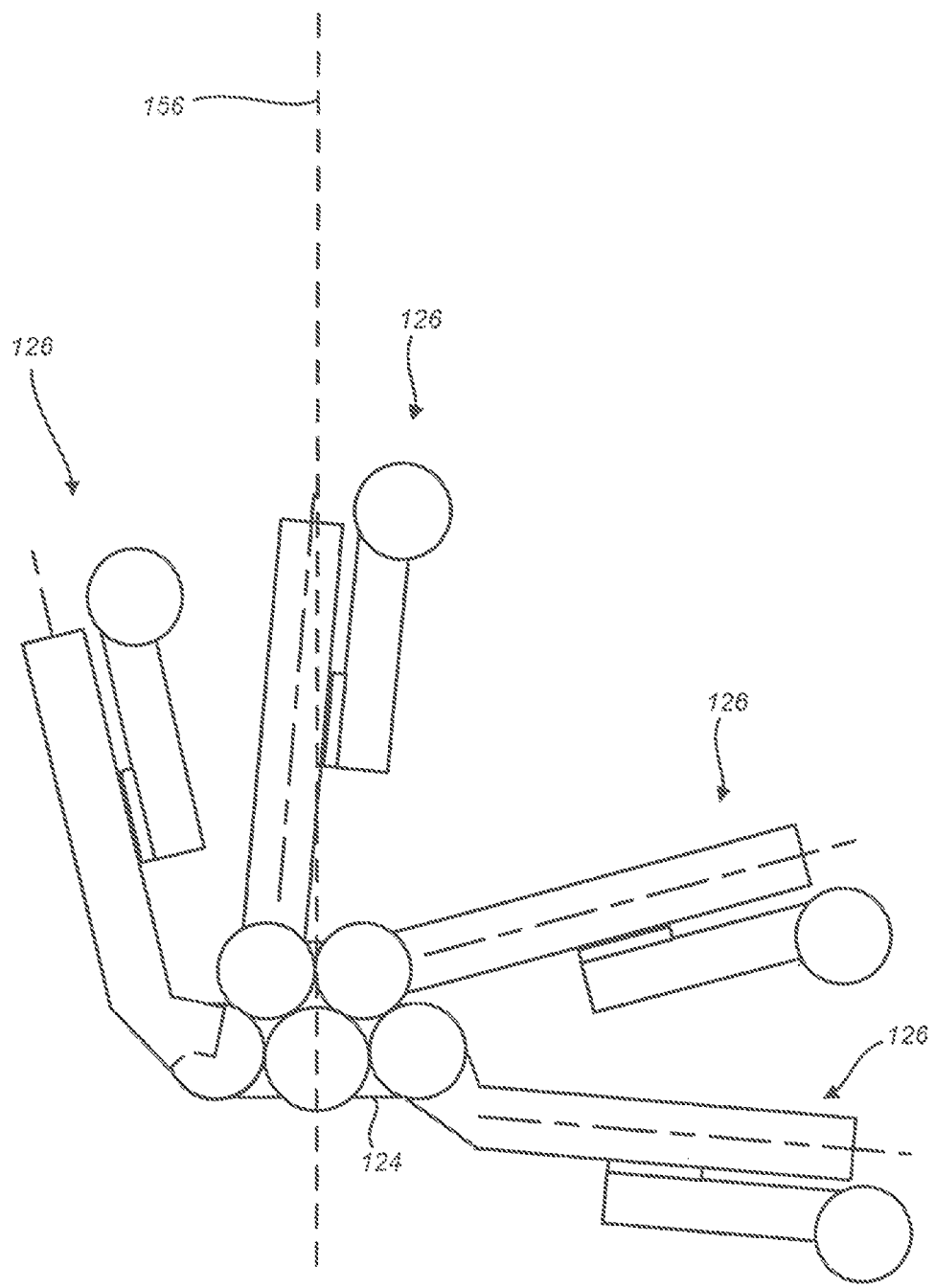
FIGS. 9A-9C illustrate rotational orientations of set-up linkages relative to an orienting platform of the robotic surgery system of FIG. 8.

FIG. 9A illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction. In one aspect, an orientation in which the set-up linkages are positions near or at their associated limits, such as shown in FIG. 9A, may be suitable for a deployed configuration for initial set-up since this positioning allows a patient-side assistant easy access to each of the arms so as to facilitate replacement of a tool in one or more manipulators or to manually position one or more tools relative a patient on a surgical table.

Figure 9B:
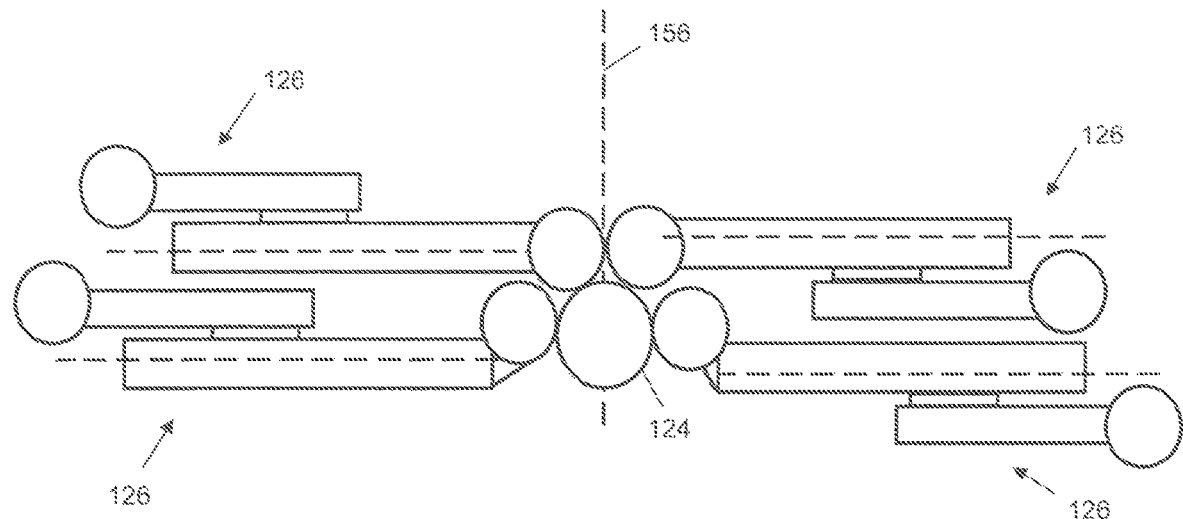
Figure 9C:
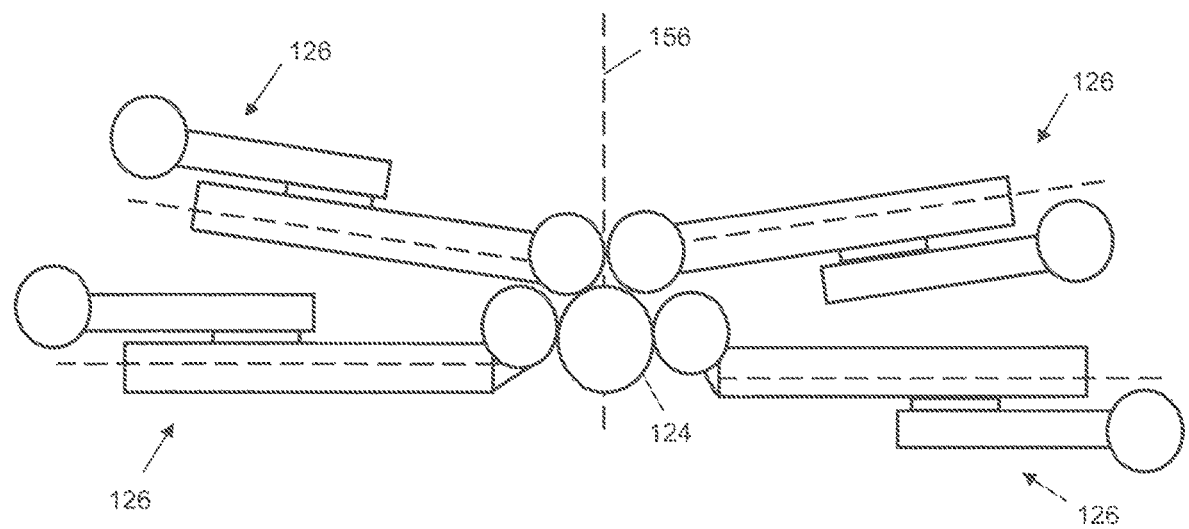

FIGS. 9B-9C illustrate configurations in which orientations and positioning of the set-up linkages are such that the manipulators are contracted and positioned near or adjacent one another. Such an orientation may be suitable for a stowed configuration in which the manipulators occupy less of the workspace. This may allow the patient-side assistant additional clearance to adjust the surgical table or to position a patient on the surgical table. In certain aspects, the system may utilize a partially stowed configuration (e.g. a sterile stow), such as shown in FIG. 9C, in which set-up joints are positioned and oriented so that the manipulators are near enough to occupy less of the workspace but far enough from each other to allow clearance for any surgical drapes that may be positioned on one or more of the manipulators. This sterile stow configuration may be effected in response to a detection of one or more components of the system being in a sterile state, which may be indicative of the presence of surgical draping on the sterile component. In another aspect, the system may utilize a fully stowed configuration (e.g. full stow), such as shown in FIG. 9B, in which the set-up joints are positioned and oriented so that the arms are contracted against or immediately adjacent one another so as to substantially minimize the workspace occupied by the manipulators.

Controlling Passive Movement of Set-Up Joints

In one aspect, a desired configuration of the setup structure of the system can be realized by controlling passive movement of the setup joints as described above. While in certain applications, this is effected by allowing the setup joints to float freely and manually moving the set-up joints to desired locations, this process can become complex and time-consuming, particularly in set-up structures that are highly configurable and include multiple robotic arms having redundant degrees of freedoms. To improve the ease and use and efficiency in using set-up joints having passive movement to achieve a desired configuration, methods, in accordance with aspects of the invention, control passive joint movement by coordinated braking of the passive joints in conjunction with actively driving certain other joints of the set-up structure. In certain aspects, reference states of the set-up joints are determined that correspond with a desired configuration of the set-up structure and joint state sensors are used to determine a displacement of the set-up joints from the reference state. One or more other joints of the set-up structure are actively driven so as to drive the set-up structure and impart forces and/or moments on the linkages associated with the set-up joints. Passive movement of the set-up-joints is inhibited by joint brakes as the platform linkage begins accelerating so that the linkages act as rigid bodies. When the force and/or moments on the linkages are such that passive movement of the set-up joints would move towards the reference state, then the brakes are released, at least in part, so as to facilitate passive movement of the joint caused by the inertia of the forces and/or moments on the linkage. In one aspect, the brakes of a particular set-up joint are released when the force and/or moments on the associated linkages are above a threshold magnitude such that inertia of the moving linkage propels or "flings" the respective linkage effecting joint movement in the desired direction.

In certain aspects, the control method selectively applies the brake on the passive joints based on the inertial forces on the joint from the forces and/or moments on the associated linkages imparted by driving of the set-up structure through one or more driven joints. In one aspect, the passive joint is braked when the inertial forces on the joint would result in passive movement that moves the passive joint away from a reference state and is allowed to float when the inertial forces on the joint would result in passive movement toward the reference state. In one aspect, since the passive movement of the joint effected by the inertial forces may not be sufficient to completely move the passive joint to a desired reference position, the one or more driven joints may be cycled until the passive movement of the passive joint provided in response effects the complete movement. Given that the various driven joints of the set-up structure each has an associated joint limit or range of joint movement, one or more driven joints can be driven a pre-determined displacement in one direction and then reversed and driven in the opposite direction. Since a particular magnitude of forces and/or moments may be needed to provide sufficient inertia to effect the requisite passive movement of the joint, the required forced and/or moments on the robotic arm can be determined by controlled driving of one or more motor driven joints according to a calculated movement, such as a shimmying movement or various other movements that result in the desired forces needed to effect passive joint movement. For example, for example, driving each of two revolute joints having parallel axes disposed in series along a kinematic chain with a particular torque would result in a larger inertial forces and/or moment in a more distal linkage of the chain than would applying that torque in the same direction to either one of the two driven revolute joints alone. Using combined movements of driven joints may be useful to overcome limitations in the torque capability or range of joint motion of more proximal joints. In another aspect, larger inertial forces and/or moments could be achieved by accelerating the more proximal linkage over a larger joint displacement or by increased acceleration.

In certain aspects, the brake release is timed to allow the passive joint to float and passively move in response to sensing of a torque on the passive joint within a particular range. For example, the brake may be released when the sensed torque is above a minimum threshold to allow for increased inertia on the joint to achieve a higher joint velocity or acceleration and may be applied, at least partially, when the sensed torque is above a maximum threshold so as to prevent excessively high velocities or acceleration of the joint during passive movement. The joint brake may be applied to maintain the reaction torque at the maximum value so as to maintain the velocity of the joint at a substantially constant velocity during passive movement or variable braking may be applied so as to provide substantially constant deceleration of the joint during passive movement as the joint nears the desired reference state. In certain aspects, the application of the brake is based, at least in part, on the sensed torque on the passive joint and a displacement of the actual joint state from the desired reference joint state (e.g. an error). This approach allows for control over the velocity and/or acceleration of the passive joint during passive movement based on how far the joint is from the reference state. For example, when the joint is above a pre-determined displacement from the reference joint state, application of the brake is controlled to provide a substantially constant joint velocity of the passive joint (when the passive joint is moving towards the reference), and when the joint displacement is sufficiently near the reference (e.g. within the pre-determined displacement), variable braking is applied to provide substantially constant deceleration until the joint reaches the desired reference state.

In one aspect, once the passive joint reaches the desired reference state, the brake is fully applied to lock the passive joint at the reference state. In another aspect, the system may apply the brakes partially, even to particularly joints at the desired reference state, until all passive joints associated with the respective robotic arm, or until all passive joints associated with the set-up structure are substantially at or near their respective reference states. This approach may prevent or reduce the substantial reaction torques that may occur in proximal joints of the set-up structure were the multiple robotic arms allowed to swing as rigid bodies during back-and-forth, alternating movement of the operating platform or other linkages of the set-up structure. The magnitude and sense of the force and moments can be determined utilizing joint state sensors, or torque sensors. Releasing of the joint brake when the sensed force and/or moments are at or above a minimum threshold, results in increased inertia associated that effects larger and/or faster passive joint movements. Alternatively, by applying the joint brake if the sensed forces are above a maximum threshold, passive joint movement that is excessive or unnecessarily fast can be avoided. In some aspects, the system determines a velocity and/or acceleration of the passive joint in response to the force and/or moment by sensing a reaction torque on the passive joint.

Each of the above example configurations, deployed, sterile stow and full stow, may be effected by controlling passive movement of particular set-up joints to certain reference states, typically a position and/or orientation of the set-up joints. While certain embodiments refer to one or more set-up joints, it is understood that any of the aspects described herein can be applied to any linkage having a joint capable of providing passive movement and can be used to control the passive movement of such a joint to achieve a desired state (e.g. position, orientation, velocity and/or acceleration). While typically, as described herein, the one or more driven joints are more proximal to the passive joints being controlled, it is appreciated that movement of one or more drive joints more distal of a passive joint may induce reaction forces in the passive joint sufficient to control movement of the passive joint (e.g. such as in a swing pumping type mechanism); however, it is generally more efficient to utilize one or more driven joints proximal of the passive joint to induce a flinging type motion of more distal joints, the inertia of which is used by selective braking to move the passive joint to the desired state.

To further illustrate the concepts described above, certain aspects are described in further detail in the following examples.

Figure 10A:
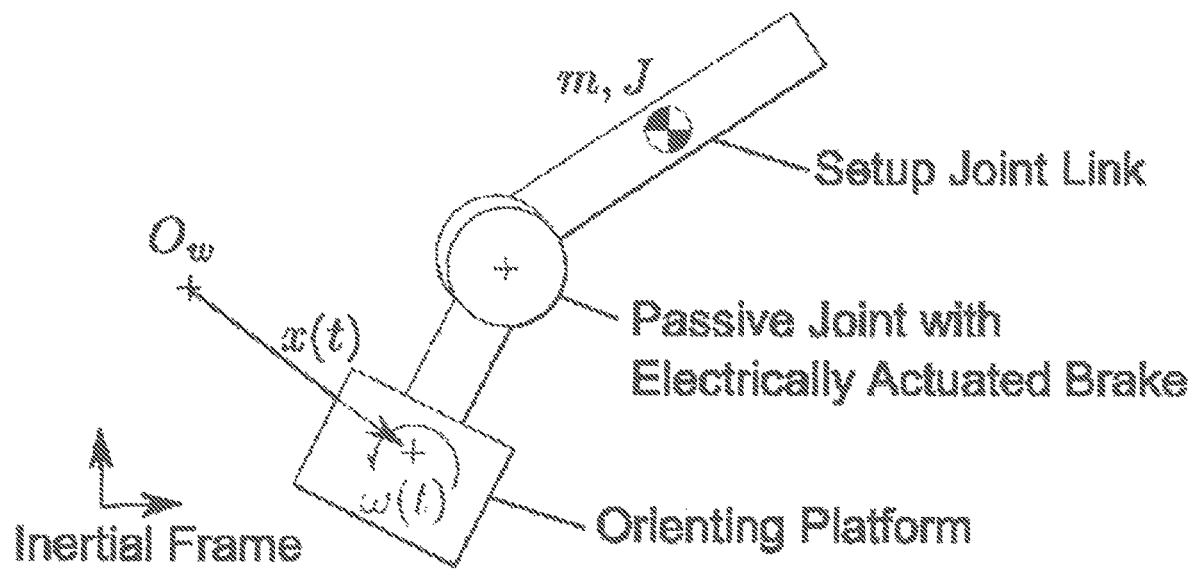
FIGS. 10A-10B illustrate a setup joint linkage and associated orienting platform, in accordance with some embodiments.

FIG. 10A illustrates a simplified 2-D diagram of a set-up joint to an orienting platform the position and orientation of which is controlled by a motor driven joint. The set-up joint is a passive joint capable of providing passive joint movement and a joint brake capable of selectively braking passive joint movement, either partially or entirely. While the joint brake is applied to the set-up joint, as the orienting platform moves, the set-up joint link translates and rotates with the orienting platform as a rigid body. When the joint brake is released, motion of the set-up joint link is governed by inertial parameters of the setup joint link (m and the acceleration of the orienting platform and friction at the setup joint.

Figure 10B:

FIG. 10B illustrates a free body diagram of the setup joint link of FIG. 10A with the joint brake released. If friction at the joint is omitted for simplicity, then the acceleration of the frame generates a force and moment proportional to the translational and rotational terms, respectively, and opposite in sense. Moments on the linkage may be summed about the joint to determine the passive acceleration with the joint brake released. The translational component of acceleration contributes a torque $ma(t)L \sin(\theta(t))$ and the rotational acceleration component contributes $J(\alpha_b(t))$.

In one aspect, the joint brake is electrically actuated, such as by a voltage signal input. The joint may be configured to partially engage in proportion to the magnitude of the voltage input. This configuration allows the voltage control of the brake to be determined by using a known curve that relates the braking force to voltage to Newton-meters of Torque, so that the brake can utilized in a similar manner as a torque motor that can only be controlled in one torque direction. In addition, because the inertial forces may be insufficient to provide enough torque to effect a desired movement of the joint to the reference state, more proximal linkages (e.g. orienting platform linkage) may be driven back and forth according to a cycled movement so that the brake can be selectively released when the induced torque is of a suitable magnitude and direction to effect passive joint movement toward the reference state in each cycling until the joint is at the reference state. Thus, the passive movement of the joint is controlled by selective braking coordinated with driven movements of one or more actively driven joints along the kinematic chain.

Figure 11:
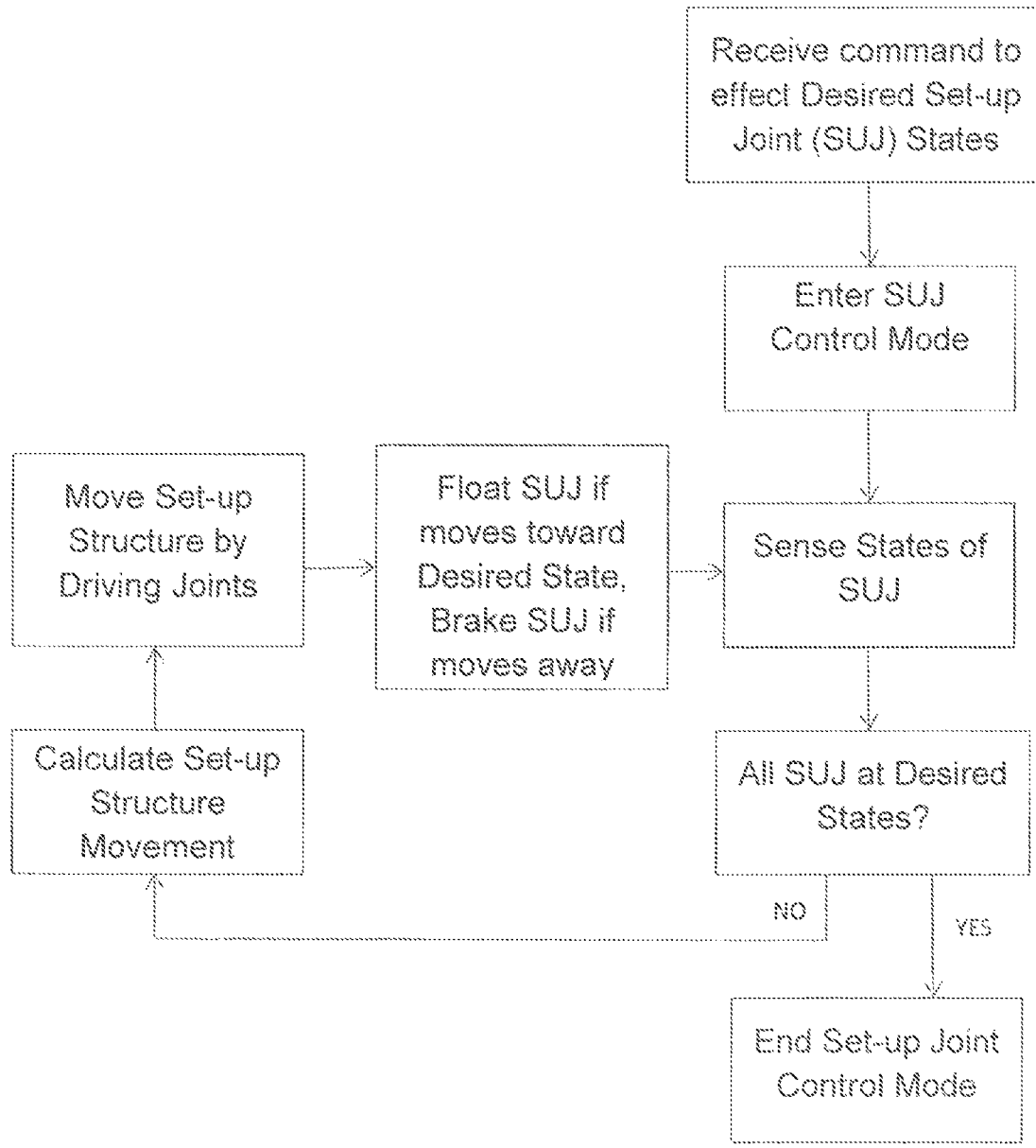
FIG. 11 is a flow chart schematically illustrating a method for preparing a robotic surgical system for surgery by driving an orienting platform of a set-up structure to move one or more passive set-up joints to a desired state, in accordance with some embodiments.

FIG. 11 schematically illustrate an example method for controlling movement of set-up joints (SUJ) of a robotic arm by driving an associated set-up structure with one or more driven joints. In response to receiving a command from a user to effect desired set-up joints states, which typically correspond to a desired pose or configuration of the robotic arm, the system enters a set-up joint control mode. The system determines the current states of the set-up joints, such as by use of joint state sensors, and if the set-up joints are not at the desired state, a set-up structure movement is calculated that may be used to move the set-up joints to the desired state through control of passive joint movements. For example, if the set-up joints are displaced from a desired state along one or more degrees of freedom, then a movement of the set-up structure may be calculated along corresponding degrees of freedom so as to impart force and/or moments to the linkages associated with the set-up joints that can be exploited to move the passive set-up joints to the reference states. The set-up structure is then driven according to the calculated movement by driving one or more motor driven joints supporting the set-up structure. During such movement, when the passive joint movement of any of the set-up joints (if allowed to move) is toward the desired reference state, then the joint is allowed to float by partially or fully releasing the joint brake for those particular set-up joints. If during the set-up structure movement, passive movement of any of the set-up joints (if allowed to move) is zero or directed away from the desired states, then the joints are braked. The joint states of the set-up joints are assessed again, and if any of the set-up joints are still not at the desired states, the process is repeated for any such joints until the system determines that all set-up joints are at the desired states, at which point the control mode is ended. In many such embodiments, such as in the manipulator structures described herein, this entire process occurs in less than a minute, often in about 10 seconds or less. The time in which the process occurs, however, varies of course according to the kinematics of a particular system, as well as the acceleration and the associated joint displacements. In one aspect, the method in FIG. 11 may include a second path of execution, such that there is one for the SUS and another for the SUJ, that synchronize at the end. Between the two SUS and the SUJ the torque demand is passed to the SUS to help smooth out its motion and the SUS acceleration is transmitted back to the SUJ to determine whether and when to release or apply brakes.

In certain embodiments, if all the set-up joints do not arrive at their associated reference states within a certain period of time of performing the described method, such as about 20 seconds, then the method may be ended. A notification may be provided to the user that not all joint are not at the desired reference states and, optionally, may identify which joints remain displaced from their associated reference states. A user may then manually articulate the set-up joints into the associated reference states or may drive one or more of the manipulators or the set-up structure into another configuration and re-enter the mode and run through the process again. In some systems, there may be certain configurations which may inhibit passive movement of certain set-up joints, such as due to lack of clearance or collisions between manipulators. In such cases, where such configurations can be identified, the methods may include automatically driving the set-up structure or one or more manipulators away from such configurations before attempting controlled movement of passive joints as described herein.

In certain aspects, the described methods may be utilized in one or more modes to control passive movement of one or more joints of one or more robotic arms to a desired references state that correspond to one or more desired arrangements of the manipulators or set-up structure. The reference states typically corresponding to a desired configuration of the robotic arms. For example, when a particular robotic arm is at a desired configuration (e.g. a deployed, stowed, sterile stow), each passive set-up joint of that arm has a particular reference state (e.g. location). In addition, the reference state of each joint may include a reference velocity and/or acceleration as the joint moves to the location of its desired state. Each mode may be entered by pressing a button that effects automatic movement of the driven joints and control of passive movement of the joints to the desired reference states without additional inputs or manual manipulation by a user.

Figure 12A:
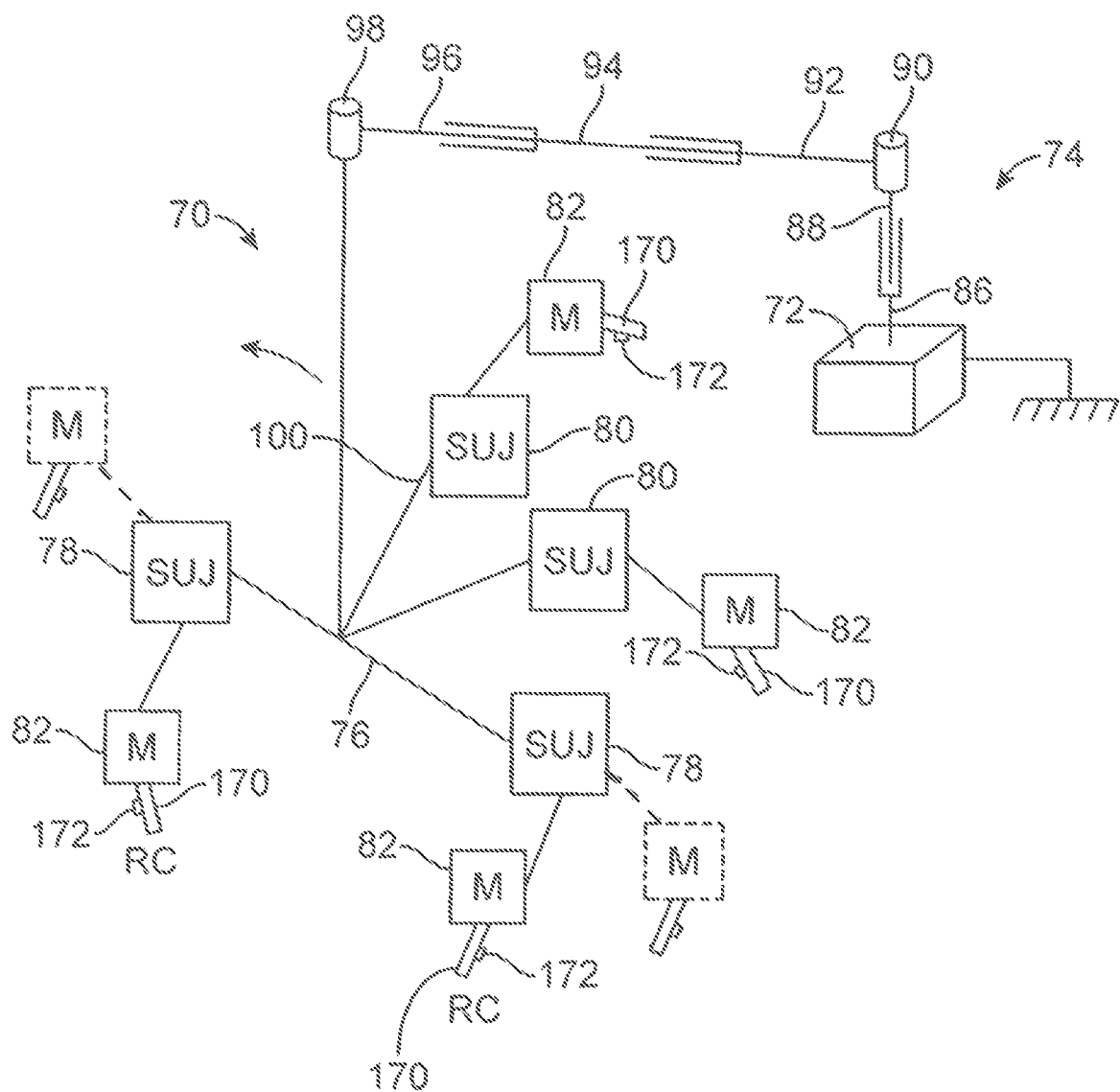
FIG. 12A is a perspective schematic representation of movement of an orienting platform supported by a cart-mounted set-up support structure that provides a desired alignment of a plurality of manipulator arms by controlling passive movement of one or more set-up joints of the system through selective braking, in accordance with some embodiments.

FIG. 12A schematically illustrate a method for driving the orienting platform to effect movement of a set-up joints 78 of each of a first manipulator associated with tool 170 and of a second manipulator 82 associated with a tool 172. The reference state of each set-up joint corresponds to a position of the manipulator and respective tool that is contracted to a position (shown in dashed lines) that allows more clearance between the respective manipulators by controlled passive movement of a set-up joint of the robotic system. It is understood that a reference state of the set-up joint may correspond to any number of configurations of the manipulators, as well as various positions, velocities, and/or accelerations of the set-up joint itself in relation to the workspace or in relation to various other joints of a particular manipulator or between manipulators. In one aspect, the system includes various modes in which the methods described herein can be used to control passive movement of the set-up joints to move the set-up joints to any number of reference states to effect a desired movement, configuration or pose of the manipulators or associated set-up structure. The term "manipulator" as used herein refers to a robotic arm which may be used to manipulate a surgical instrument or may include various other robotic arms, such as may be used in an endoscope or for various other tools.

Calculation of Orienting Platform Movement Commands

In one aspect, the passive movement of the set-up joints is effected by the inertial forces and/or movements imparted to the linkages by movement of the set-up structure achieved by driving of one or more driven joints, typically joints that are upstream of the set-up joints. In one aspect, movement of the set-up structure is provided by a calculated movement of the orienting platform in one degree of freedom, typically a back-and-forth pivoting movement of the orienting platform 124 about a vertical revolute axis using a drive system, as described in further detail in the examples below. In another aspect, since the methods exploit favorable joint movement of passive joints and inhibit unfavorable movement so as to achieve a desired reference state of the passive joints, the movement of the orienting platform is not required to be customized according to any particularly configuration of the manipulators. Advantageously, an entirely automatic movement of the orienting platform (e.g. back-and-forth rotation that accelerates the orienting platform back and forth) can be used in any of the methods described herein, in controlling movement of passive joints toward desired reference states to achieve any number of manipulator or set-up structure configurations.

Figure 12B:
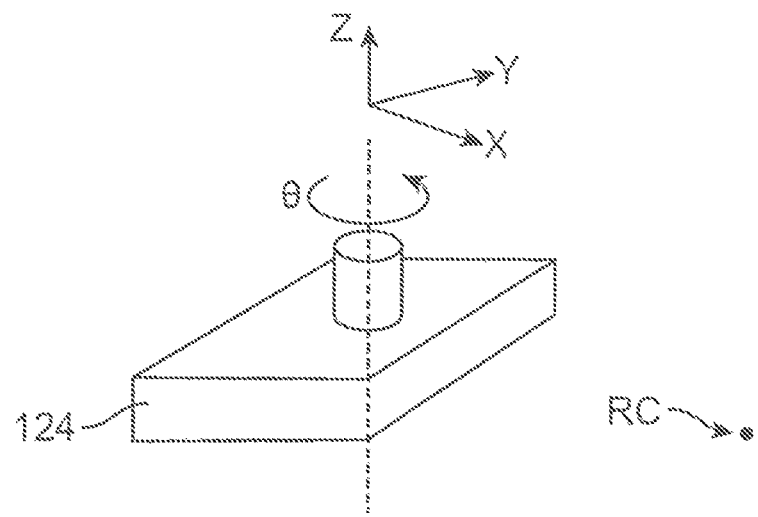
FIGS. 12B and 12C are a schematic representation of an orienting platform showing an associated coordinate system and degrees of freedom; and a perspective representation of an orienting platform supported by a ceiling gantry set-up support structure so as to provide a desired alignment of a single manipulator arm with an associated surgical access site, in accordance with some embodiments.
Figure 12C:
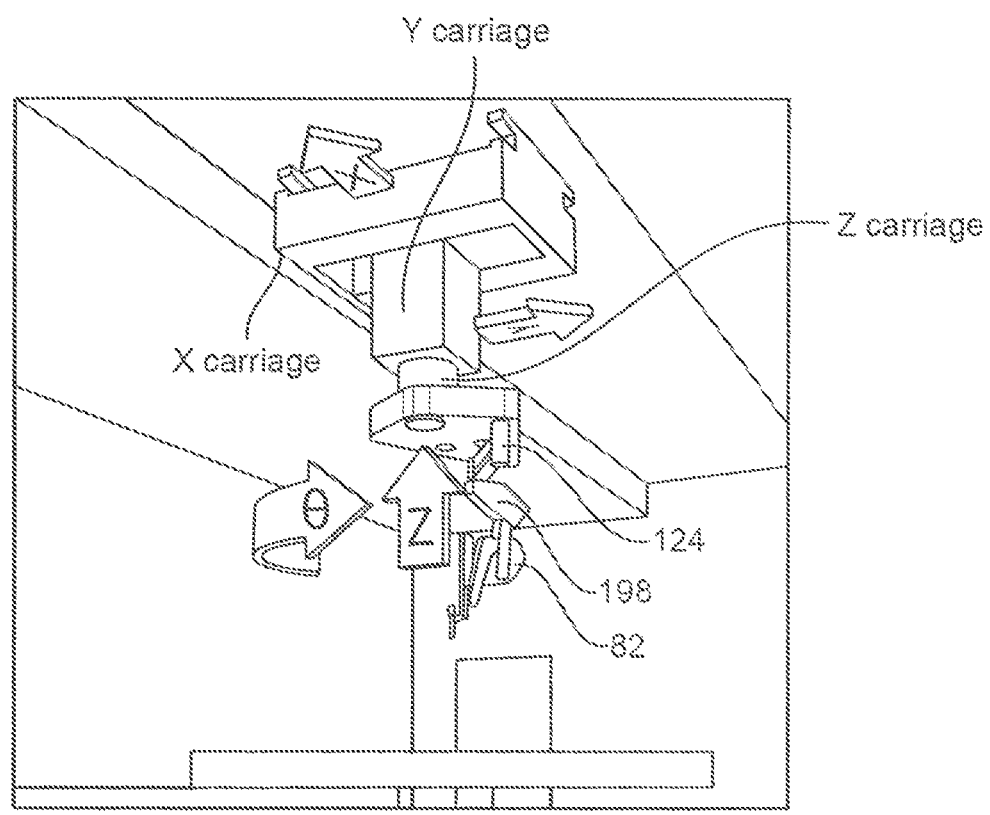

FIG. 12B-12C depict a drive system for orienting platform 124 that allows movement of the set-up structure along x, y, and z axes. By moving driving one or more motor driven joints to generate velocities and/or accelerations along one or more directions along the x, y, z and 0 axes, corresponding movements in linkages associated with a set-up joint 198 can be effected that result in passive movement of the set-up joint 198. Along with orienting platforms supported by cart-mounted set-up structures such as those described above, ceiling mounted set-up structures 190 and other driven robotic linkages with one, two, three, four, or more degrees of freedom may be employed. Hence, while the systems may be described with reference to a few exemplary robotic kinematic structures, the control techniques may apply well to a range of other robotic systems having redundant degrees of freedom and/or large numbers of joints, and are particularly interesting when considering such systems that have a mix of active and passive joints; systems with one set of joints that are driven during set-up and another different set (with or without some overlapping members) of joints that are driven during surgery; systems in which individual manipulator controllers exchange only limited state information; and the like.

In one aspect, to use the robotic capabilities of the system during set-up, the processor of the robotic system may include software implementing a mode in which the robotic structure is driven toward and/or maintains a desired relationship or pose between the orienting platform and the manipulator remote center during the passive joint control modes described herein. This algorithm, when active, takes as its inputs the actual and desired relationships between the orienting platform and the manipulator remote center and drives the actual pose to the desired one, optionally without disturbing the position and orientation of the manipulator remote center. In other words, as the passive joints move, the active axes may optionally follow in such a way so as to achieve or maintain a specific robot pose.

In another aspect, a mode in which movement of passive joints are controlled as described herein, may include multiple sub-modes or variations in how these concepts are applied based on one or more variables or attributes of the system. For example, passive movement may be controlled according to a particular method when the passive joints are at a substantial displacement from the desired reference state (e.g. FAR mode) and may be controlled according to another method when the passive joints are sufficiently near the desired reference state (e.g. NEAR mode). For example, larger movements or faster accelerations of the orienting platform linkage, which allows for larger and/or faster passive movements, may be used when the joints are displaced from their respective reference states greater than a pre-determined displacement. In turn, smaller movements or slower speeds and accelerations of the orienting platform linkage may be used when the set-up joints are sufficiently close to their desired states to allow for more fine tuned passive joint movements and avoid excess reaction torques on more proximal joints supporting the set-up structure.

In one aspect, the "reference" or "target" position for the setup joints in shimmy FAR mode, refers to the reference joint position without shimmy motion of the SUS. The idea is to hover near the final target position without locking up. If the reference were the raw joint position, the controller would effectively chase the position back and forth during each shimmy cycle of the SUS. In one approach, the joint error induced by the SUS shimmy can be effectively removed by notch filtering at the frequency of the sinusoidal motion. It is appreciated, however, that this effect may be achieved in various other ways. In contrast, in Shimmy NEAR mode, the joint position may be targeted without any compensation as we want to accurately target at a particular joint configuration.

Figure 13:
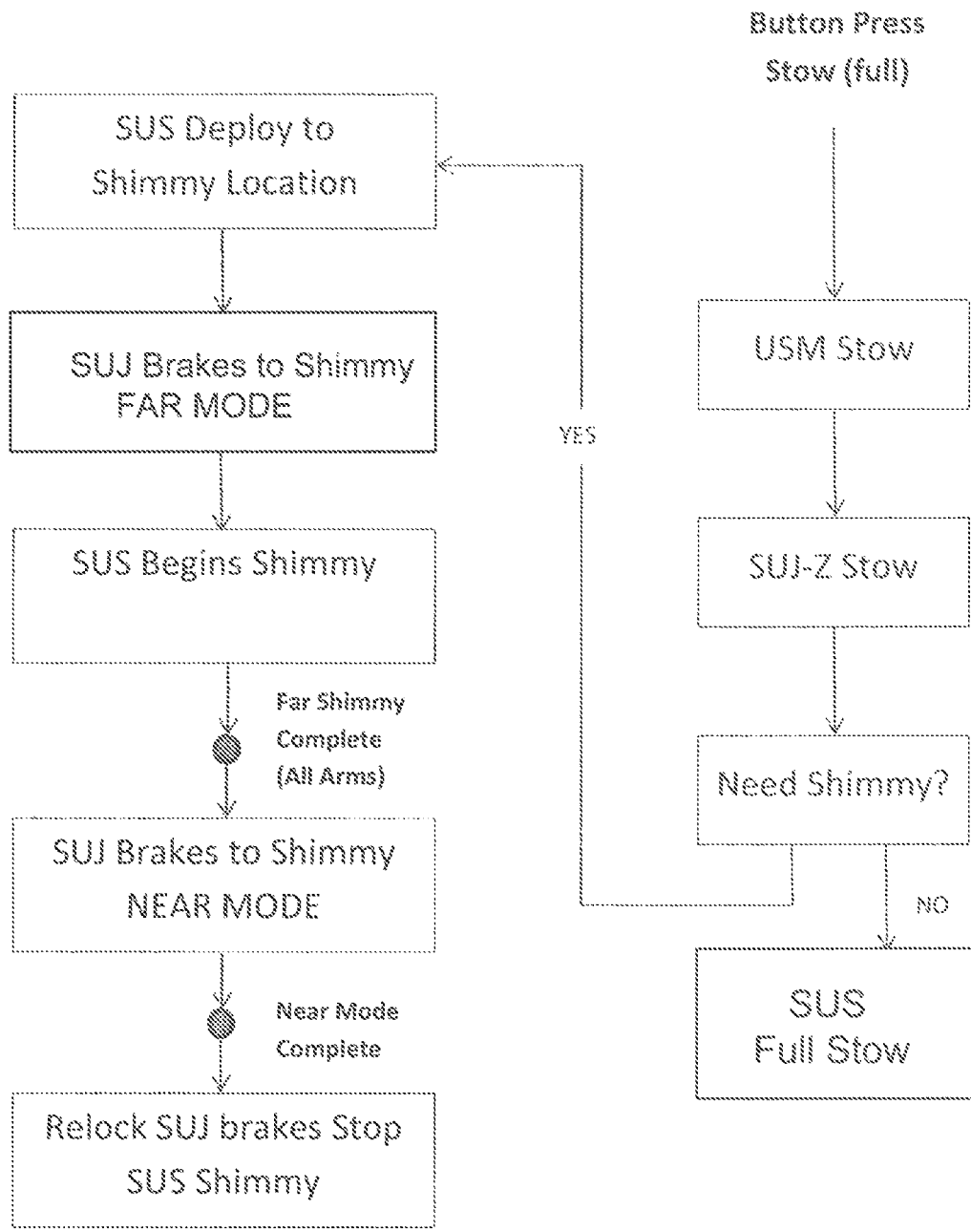
FIG. 13 schematically shows a method of controlling passive set-up joints supported by the orienting platform by modes providing a shimmy movement of the orienting platform, in accordance with some embodiments.

FIG. 13 illustrates an under-actuated joint control mode utilizing two such sub-modes that differ based on a displacement of the set-up joints from the reference states (FAR mode and NEAR mode). As shown in FIG. 13, after a user presses a button to effect a full stow configuration, each of the universal surgical manipulators (USM) moves by driven joint movements to configurations suitable for being stowed. The Set-Up Joint along the vertical axis (SUJ-Z) is actuated to the top most position of its range. The system then senses the joint states of the Set-up Joints (SUJ) and determines whether the system needs to move the SUJ joints by an alternating movement of the orienting platform, referred to herein as a "shimmy." If no shimmy is required, then the Set-Up Structure (SUS) is fully stowed (typically completed by retracting the horizontal boom toward the vertical support column at the base). If the system determines that the SUJ joints need to be adjusted, then the SUS deploys to the shimmy location. When deploying the SUS to shimmy, the orienting platform should be positioned such that the manipulators have sufficient clearance from a more proximal support column on the base of the system, but not extended further than necessary to avoid excessive reaction torques on more proximal joints during the shimmying movement. The SUJ brakes are applied so that the shimmying movement of the orienting platform imparts forces and/or moments through the manipulator and set-up joint linkages as a rigid body so that when the joints are subsequently released, the inertial forces and/or moments are sufficient to fling or move the set-up joints to the reference states in an efficient manner. The SUS then begin shimmying and the resulting passive movement of the SUJ are controlled through selective braking of each SUJ, as described herein, until all SUJ are within a threshold displacement from their associated reference states. The system then switches to a near mode, in which the SUS shimmy has a smaller acceleration or by a smaller alternating joint displacement, since less movement of the SUJ is required to reach the desired reference state. This allows for more fine tuned movements as the SUJ reach their respective reference states, after which the SUJ brakes are locked and the SUS shimmy is ended. As the SUJ joints are now locked at their respective reference states, the SUS can be fully stowed by horizontal retraction of the boom.

In one aspect, the brake of the joint providing passive movement is controlled by a joint brake controller so as to apply a sensed torque induced in the joint by passive movement in a similar manner as a typical motor torque controller. This approach is advantageous as it may be utilized in a system having conventional motor torque controller, such as a proportional derivative controller, by modifying a control feature of the joint brake, such as through additional software. This approach is detailed further in FIG. 14A, FIG. 14B (the detail of box A in FIG. 14A) and FIG. 14C (the detail of box B shown in FIG. 14B).

Figure 14A:
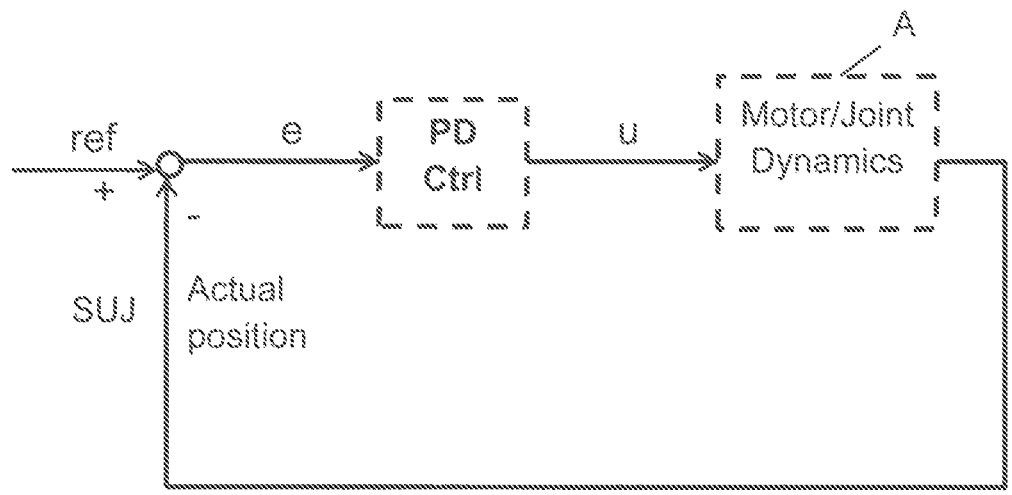
FIGS. 14A-14C schematically show control diagrams for controlling movement of a passive joint by use of a motorized control input, in accordance with some embodiments.

FIG. 14A illustrates a feedback control loop in which the passive movement of the set-up joint is controlled with a Proportional Derivative Controller (PD Controller), similar to its use in a conventional motorized joint control loop. $B_m$ is the maximum brake torque/force for a configured limit, while E is a velocity threshold below which the brake should remain released. The system determines an error (e) of the set-up joint by comparing the reference state to its actual position, which is input into the PD controller, which then calculates the control signal (u) to effect the joint torque needed to achieve the reference state. In a conventional motor driven joint, the "u" signal would be input into the motor joint dynamics control so as to drive an associated joint motor with the requisite torque to the reference state. In a passive joint, however, the joint is incapable of being driven. Due to movements of various other linkages of the kinematic chain, forces and/or moments imparted to linkages associated with the passive joint produce torques within the passive joint that may be used to effect passive movement that moves the joint to the desired reference state.

Figure 14B:
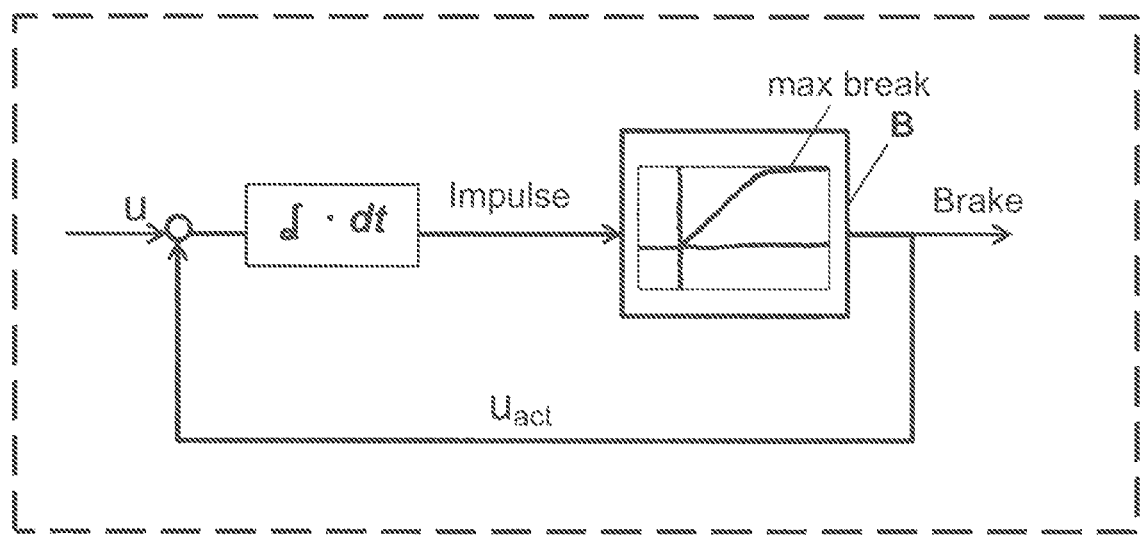

FIG. 14B illustrates a brake control loop that simulates the motor/joint dynamics in a conventional motor driven joint (detail of box A in FIG. 14A) for use in controlling passive movement by selective application of a joint brake. In the brake control loop in FIG. 14B, the motor torque control signal is compared to the actual torque sensed in the set-up joint, then integrated to obtain an impulse over time, logic is applied that evaluates the direction or the sign of the velocity(v), (sign (u)=−sign (v)), and if the sign of (v) is in the direction towards the reference, then the torque present in the joint is depleted by release, or partial release of the joint brake over a period of time. Since the torque present in the joint due to passive movement may be (and often is) less than that required to move the joint to the reference state, this loop may be repeated multiple times with each cycling of the orienting platform by driving of the joints. This cycling of the orienting platform may be referred to as a "shimmy" movement effecting by driving a joint of the platform linkage continuously back-and-forth in opposite direction (such as by using a sinusoidal signal input) so that the orienting platform moves back and forth accelerating between a positive displacement and a negative displacement. The joint brake control loop described above exploiting the torques produced in the set-up joints by passive movement with each cycling or shimmy of the orienting platform until the set-up joint reaches the reference state, at which point the brake is applied to lock the set-up joint in place. It is understood that in system having multiple set-up joints, each having an associated joint brake controller used to control passive movement as described above, that during movement of the orienting platform in one direction certain set-up joints may be floating while certain other joints may be braked.

Figure 14C:
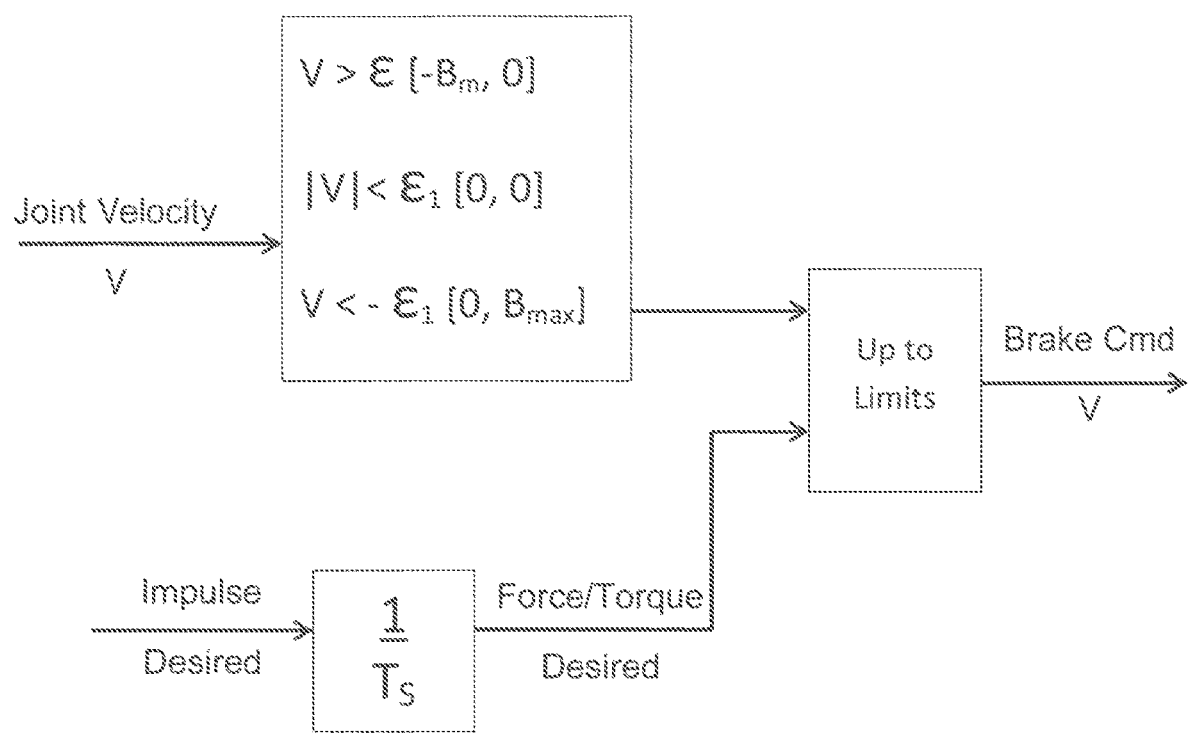

FIG. 14C illustrates a detail of Block B in FIG. 14B, in example in accordance with aspect of the invention. Block B includes a block that determines the physically achievable braking (one-sided) given the joint velocity and another block that clips a force or torque request against the available braking effort. Note that the desired impulse is divided by Ts, the sample rate of the control-system (e.g. 0.75 ms), to find a force or torque that would satisfy the entire impulse in one control loop. The limit Bm may be the maximum brake friction but is typically tuned down to a lower value to reduce the load imparted on the SUS. The epsilon threshold forces the braking effort to zero whenever the joint velocity is small, thereby preventing the joint from locking up in Shimmy FAR mode.

Figure 14D:
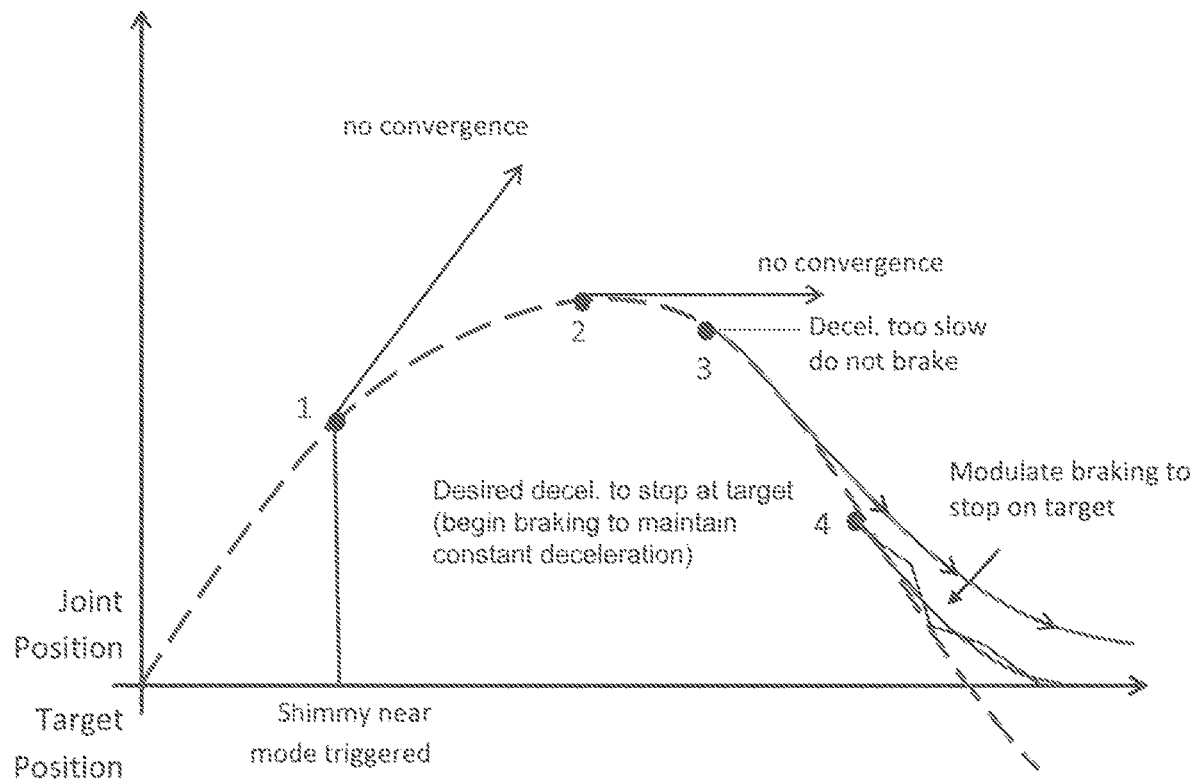
FIG. 14D graphically illustrate braking control mechanisms by which to effect a calculated joint torque corresponding to the motorized control input, in accordance with some embodiments.

In certain aspects, the logic applied in determining application of brake force may apply selective braking or variable braking along a continuous spectrum up to a max brake value. Applying variable braking allows the joint brake to achieve more controlled movement of the passive set-up joint. For example, as shown in the graph of FIG. 14D depicting braking force versus joint state of the set-up joint, as the torque induced in the passive set-up joint changes in direction during back-and-forth shimmy of the supporting orienting platform, a varying braking force allows the passive joint to move at a substantially constant velocity when the passive joint is moving. In addition, the logic may apply variable braking force to achieve various other controlled movements, such as to provide constant deceleration of the set-up joint when moving toward the reference state and the set-up joint is sufficiently near the reference state (e.g. within a threshold displacement). In certain embodiments, the constant velocity control feature is used in a "Shimmy Far Mode" when the set-up joint displacement is above a displacement threshold (t) and the constant deceleration control feature is used when displacement of the set-up joint from the reference is within the threshold, as shown in FIG. 14D.

FIG. 14D shows the stages of shimmy near mode in an example in accordance with aspects of the invention. When sinusoidal error plotted with a dashed line is the unbraked trajectory relative to the target position. At points 1 and 2, the tangent does not intersect the x-axis at any point in the future so there is no constant deceleration profile. At point 3, the constant deceleration to converge to the target is less than desired and would be below the controllable brake effort levels. At point 4, the constant deceleration to converge matches a tunable desired value in the software and brake application begins. The brakes are then modulated to stop at the target—which notably provides a smooth parabolic trajectory with its vertex at zero and the deviations above and below this trajectory as the controller modulates the brake. This decision making by the controller in this diagram provides braking at a point that allows a stop with comfortable deceleration and modulating the brake to stop at the desired position.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A robotic system comprising:
   a first robotic arm comprising a first joint;
   a link supporting the first robotic arm;
   one or more driven joints supporting the link; and
   a processor operatively coupled to the one or more driven joints, wherein the processor is configured to:
   accelerate the link by driving the one or more driven joints and imparting a force or moment to the first robotic arm,
   inhibit a passive movement of the first joint when the passive movement of the first joint operates to cause the first joint to move away from a reference state of the first joint, wherein the passive movement of the first joint is responsive to the force or moment imparted to the first robotic arm, and
   facilitate the passive movement of the first joint when the passive movement of the first joint operates to cause the first joint to move towards the reference state.

2. The robotic system of claim 1, wherein the processor is further configured to:
   halt the passive movement of the first joint when the first joint is at the reference state.

3. The robotic system of claim 1, further comprising:
   a second robotic arm, wherein the reference state corresponds to a deployed configuration of the first robotic arm, wherein in the deployed configuration the first robotic arm is extended and spaced apart from the second robotic arm.

4. The robotic system of claim 1, further comprising:
   a second robotic arm, wherein the reference state corresponds to a stowed configuration of the first robotic arm, wherein in the stowed configuration the first robotic arm is contracted and disposed against or adjacent to the second robotic arm.

5. The robotic system of claim 1, wherein the processor is further configured to:
   determine at least one of the following using a sensed torque of the first joint:
   when the passive movement of the first joint operates to cause the first joint to move away from the reference state, and
   when the passive movement of the first joint operates to cause the first joint to move towards the reference state.

6. The robotic system of claim 1, wherein:
   the first robotic arm further comprises a first joint brake operatively coupled to the processor;
   the processor is configured to inhibit the passive movement of the first joint by at least partly braking the first joint using the first joint brake; and
   the processor is configured to facilitate the passive movement of the first joint by at least partly releasing the first joint using the first joint brake.

7. The robotic system of claim 1, wherein the processor is configured to facilitate the passive movement of the first joint by:
   selectively releasing braking of the first joint to allow the first joint to accelerate to a velocity; and
   selectively applying braking to the first joint to maintain the first joint at the velocity or to decelerate the first joint.

8. The robotic system of claim 1, wherein the processor is configured to accelerate the link by:
   driving the one or more driven joints to accelerate the link in opposite directions over time.

9. The robotic system of claim 8, wherein accelerating the link in opposite directions over time imparts an inertial force or moment to the first robotic arm such that a reaction force or torque in the first joint alternates between opposing directions over time.

10. The robotic system of claim 8, wherein the processor is further configured to:
    alternate between inhibiting the passive movement of the first joint and facilitating the passive movement of the first joint until the first joint is at the reference state.

11. The robotic system of claim 8, wherein the link comprises a platform supporting the first robotic arm, wherein the one or more driven joints comprises a driven revolute joint, and wherein the processor is configured to accelerate the link by driving the driven revolute joint to rotate the platform about a vertically extending axis.

12. The robotic system of claim 11, wherein the first joint comprises a revolute joint that revolves around a first joint axis, wherein the first joint axis extends vertically.

13. The robotic system of claim 11, further comprising a second robotic arm supported by the platform, the second robotic arm comprising a second joint, wherein:
    the first robotic arm further comprises a first joint brake operatively coupled to the processor;
    the processor is configured to inhibit and facilitate the passive movement of the first joint by selectively applying the first joint brake;
    accelerating the link by driving the one or more driven joints imparts a second force or moment to the second robotic arm; and
    the processor is further configured to:
    inhibit a passive movement of the second joint when the passive movement of the second joint operates to cause the second joint to move away from a reference state of the second joint, wherein the passive movement of the second joint is in response to the second force or moment imparted to the second robotic arm, and
    facilitate the passive movement of the second joint when the passive movement of the second joint operates to cause the second joint to move towards the reference state of the second joint.

14. The robotic system of claim 1, wherein the reference state comprises a joint position or a joint orientation.

15. The robotic system of claim 1, wherein the processor is configured to accelerate the link by:

driving the one or more driven joints to accelerate the link to a first speed when a displacement of the first joint from the reference state exceeds a pre-determined displacement; and
   driving the one or more driven joints to accelerate the link to a second speed lower than the first speed when the displacement of the first joint from the reference state does not exceed the pre-determined displacement.
16. The robotic system of claim 1, wherein the processor is configured to facilitate the passive movement of the first joint by:
   determining that a combination of a sensed state of the first joint and a sensed state of the link corresponds to sufficient force, moment, or momentum for the passive movement of the first joint to move the first joint to the reference state; and
   releasing braking of the first joint in response to the determination.
17. The robotic system of claim 1, wherein the first joint is an under-actuated joint.
18. A robotic system comprising:
   a first robotic arm comprising a plurality of joints and a plurality of joint brakes, each joint of the plurality of joints being configured to be braked by at least one corresponding joint brake of the plurality of joints brakes, and each joint of the plurality of joints having an associated reference state corresponding to a desired configuration of the first robotic arm;
   a platform linkage supporting the first robotic arm;
   one or more driven joints physically coupled to the platform linkage; and
   a processor operatively coupled to the one or more driven joints, wherein the processor is configured to accelerate the platform linkage by driving the one or more driven joints and imparting a force or moment to the first robotic arm;
   wherein the processor is configured to, for each joint of the plurality of joints:
      inhibit a passive movement of the joint when the passive movement of the joint operates to cause the joint to move away from the associated reference state of the joint, wherein the passive movement of the joint is in response to the force or moment imparted to the first robotic arm; and
      facilitate the passive movement of the joint when the passive movement of the joint operates to cause the joint to move towards the associated reference state of the joint.
19. The robotic system of claim 18, wherein
   the processor is configured to accelerate the platform linkage by: driving the one or more driven joints to accelerate the platform linkage in opposite directions over time; and
   the processor is further configured to, for each joint of the plurality of joints, alternate between inhibiting and facilitating the passive movement of the joint when the joint is displaced from the associated reference state of the joint.
20. The robotic system of claim 18, wherein processor is configured to accelerate the platform linkage by:
   driving the one or more driven joints to accelerate the platform linkage to a first speed when a displacement exceeds a pre-determined displacement, the displacement being of a first joint of the plurality of joints from the associated reference state associated with the first joint; and
   driving the one or more driven joints to accelerate the platform linkage to a second speed lower than the first speed when the displacement is within the pre-determined displacement.
21. The robotic system of claim 18, wherein at least one joint of the plurality of joints is an under-actuated joint.
22. The robotic system of claim 18, wherein the processor is configured to:
   facilitate the passive movement of a first joint of the plurality of joints while inhibiting the passive movement of a second joint of the plurality of joints by partially applying the corresponding joint brake of the second joint.
23. A tele-operational system comprising:
   a first robotic arm comprising a first joint and a first joint brake;
   a platform linkage supporting the first robotic arm;
   one or more driven joints supporting the platform linkage; and
   a processor operatively coupled to the one or more driven joints, wherein the processor is configured to:
      accelerate the platform linkage by driving the one or more driven joints, thereby imparting a force or moment to the first robotic arm,
      sense a joint torque of the first joint,
      determine, using the joint torque, if a passive movement of the first joint in response to the force or moment operates to cause the first joint to move towards or away from a reference state of the first joint,
      inhibit the passive movement of the first joint in response to determining that the passive movement of the first joint operates to cause the first joint to move away from the reference state of the first joint by at least partly applying braking to the first joint,
      facilitate the passive movement of the first joint in response to determining that the passive movement of the first joint operates to cause the first joint to move the first joint towards the reference state of the first joint by at least partly releasing braking applied to the first joint, and
      halt the passive movement of the first joint in response to the first joint being at the reference state of the first joint.
24. The tele-operational system of claim 23, further comprising a second robotic arm, the second robotic arm comprising a second joint and a second joint brake, wherein:
   accelerating the platform linkage by driving the one or more driven joints imparts a second force or moment to the second robotic arm; and
   the processor is further configured to, while facilitating the passive movement of the first joint, inhibit a passive movement of the second joint by at least partially applying the second joint brake when the passive movement of the second joint operates to cause the second joint to move away from a reference state of the second joint, wherein the passive movement of the second joint is in response to the second force or moment to the second robotic arm.
25. The tele-operational system of claim 23, wherein
   the processor is configured to accelerate the platform linkage by: driving the one or more driven joints to accelerate the platform linkage in opposite directions over time, wherein accelerating the platform linkage between opposite directions imparts an inertial force or moment to the first robotic arm such that a reaction force or torque in the first joint alternates between opposing directions; and the processor is further configured to: alternate between inhibiting the passive movement of the first joint and facilitating the passive movement of the first joint until the first joint is at the reference state of the first joint.

\* \* \* \* \*